(12) United States Patent
Rooney et al.

(10) Patent No.: US 7,792,591 B2
(45) Date of Patent: Sep. 7, 2010

(54) INTRODUCER FOR THERAPY DELIVERY ELEMENTS

(75) Inventors: Ethan A. Rooney, White Bear Lake, MN (US); Gary W. King, Fridley, MN (US); Thomas E. Cross, Jr., St. Francis, MN (US); Richard T. Stone, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 11/450,147

(22) Filed: Jun. 9, 2006

(65) Prior Publication Data

US 2007/0118196 A1    May 24, 2007

Related U.S. Application Data

(63) Continuation-in-part of application No. 11/374,852, filed on Mar. 14, 2006, and a continuation-in-part of application No. 11/375,492, filed on Mar. 14, 2006, and a continuation-in-part of application No. 11/374,793, filed on Mar. 14, 2006.

(60) Provisional application No. 60/689,201, filed on Jun. 9, 2005, provisional application No. 60/700,627, filed on Jul. 19, 2005, provisional application No. 60/761,823, filed on Jan. 25, 2006.

(51) Int. Cl.
*A61N 1/00* (2006.01)
*A61M 29/00* (2006.01)

(52) U.S. Cl. .................. 607/116; 604/96.01; 604/104

(58) Field of Classification Search ................ 604/116, 604/104–109, 96.01, 164.01, 523; 607/116; 606/192, 194, 200

See application file for complete search history.

(56) References Cited

U.S. PATENT DOCUMENTS 3,211,151 A * 10/1965 Foderick et al. .......... 604/97.02

(Continued)

FOREIGN PATENT DOCUMENTS

EP    0 334 116    9/1989

(Continued)

OTHER PUBLICATIONS

Kapural et al., "Occipital Nerve Electrical Stimulation via the Midline Approach and Subcutaneous Surgical Leads for Treatment of Severe Occipital Neuralgia: A Pilot Study," Anesthesia Analgesia 2005; 101, pp. 171-174.

(Continued)

*Primary Examiner*—Kevin C Sirmons
*Assistant Examiner*—Michael J Anderson
(74) *Attorney, Agent, or Firm*—Shumaker & Sieffert, P.A.

(57) ABSTRACT

The disclosure describes an introducer for facilitating implantation of therapy elements into a patient. The introducer has an elongated body that defines a lumen for advancement of a therapy element to an implant site, and includes a curved portion medially located between substantially straight proximal and distal portions. As an example, the shape of the introducer may allow a clinician to more easily, and without substantially damaging surrounding tissue, find the correct tissue depth and follow that tissue depth to the implant site. For example, the introducer may facilitate implantation of a therapy element within or between desired layers of tissue of the patient. In some embodiments, fluid may be injected through the introducer to create a space within the tissue to implant the therapy element. Fluid may also be evacuated through the introducer prior to implantation.

24 Claims, 17 Drawing Sheets

U.S. PATENT DOCUMENTS

| | | | |
|---|---|---|---|
| 3,385,300 A * | 5/1968 | Holter | 604/275 |
| 3,978,865 A | 9/1976 | Trabucco | |
| 4,058,128 A | 11/1977 | Frank et al. | |
| 4,142,530 A | 3/1979 | Wittkampf | |
| 4,177,818 A | 12/1979 | De Pedro | |
| 4,658,835 A | 4/1987 | Pohndorf | |
| 4,759,748 A * | 7/1988 | Reed | 604/95.04 |
| 5,156,592 A | 10/1992 | Martin et al. | |
| 5,255,691 A | 10/1993 | Otten | |
| 5,300,110 A | 4/1994 | Latterell et al. | |
| 5,409,469 A * | 4/1995 | Schaerf | 604/282 |
| 5,454,364 A * | 10/1995 | Kruger | 600/114 |
| 5,531,684 A | 7/1996 | Ensminger et al. | |
| 5,545,207 A | 8/1996 | Smits et al. | |
| 5,639,276 A * | 6/1997 | Weinstock et al. | 606/129 |
| 5,676,655 A * | 10/1997 | Howard et al. | 604/116 |
| 5,695,470 A * | 12/1997 | Roussigne et al. | 604/116 |
| 5,713,867 A | 2/1998 | Morris | |
| 5,788,713 A * | 8/1998 | Dubach et al. | 606/130 |
| 5,792,187 A | 8/1998 | Adams | |
| 5,807,350 A | 9/1998 | Diaz | |
| 5,868,729 A | 2/1999 | Pelfrey | |
| 6,038,480 A | 3/2000 | Hrdlicka et al. | |
| 6,058,331 A | 5/2000 | King | |
| 6,090,072 A | 7/2000 | Kratoska et al. | |
| 6,249,707 B1 | 6/2001 | Kohnen et al. | |
| 6,473,653 B1 | 10/2002 | Schallhorn et al. | |
| 6,505,075 B1 | 1/2003 | Weiner | |
| 6,517,477 B1 * | 2/2003 | Wendlandt | 600/114 |
| 6,565,594 B1 | 5/2003 | Herweck et al. | |
| 6,673,091 B1 * | 1/2004 | Shaffer et al. | 606/201 |
| 6,735,475 B1 | 5/2004 | Whitehurst et al. | |
| 6,802,807 B2 | 10/2004 | Anderson et al. | |
| 6,836,687 B2 * | 12/2004 | Kelley et al. | 607/122 |
| 6,840,899 B2 | 1/2005 | Koga et al. | |
| 6,866,044 B2 | 3/2005 | Bardy et al. | |
| 6,866,650 B2 | 3/2005 | Stevens et al. | |
| 6,978,180 B2 | 12/2005 | Tadlock | |
| 7,010,345 B2 | 3/2006 | Hill et al. | |
| 7,092,765 B2 * | 8/2006 | Geske et al. | 607/122 |
| 7,120,495 B2 | 10/2006 | Bardy et al. | |
| 2001/0049502 A1 | 12/2001 | Chen | |
| 2002/0035377 A1 | 3/2002 | Bardy et al. | |
| 2002/0035378 A1 | 3/2002 | Bardy et al. | |
| 2002/0035381 A1 | 3/2002 | Bardy et al. | |
| 2002/0103510 A1 | 8/2002 | Bardy et al. | |
| 2002/0107553 A1 | 8/2002 | Hill et al. | |
| 2002/0143369 A1 | 10/2002 | Hill et al. | |
| 2002/0165536 A1 * | 11/2002 | Kelley et al. | 606/41 |
| 2002/0165537 A1 * | 11/2002 | Kelley et al. | 606/41 |
| 2002/0165586 A1 | 11/2002 | Hill et al. | |
| 2002/0198572 A1 | 12/2002 | Weiner | |
| 2003/0004549 A1 | 1/2003 | Hill et al. | |
| 2003/0028147 A1 | 2/2003 | Aves et al. | |
| 2003/0036787 A1 | 2/2003 | Redko et al. | |
| 2003/0078633 A1 | 4/2003 | Firlik et al. | |
| 2003/0114908 A1 | 6/2003 | Flach | |
| 2003/0144709 A1 | 7/2003 | Zabara et al. | |
| 2003/0158545 A1 | 8/2003 | Hovda et al. | |
| 2003/0212445 A1 | 11/2003 | Weinberg | |
| 2004/0015204 A1 | 1/2004 | Whitehurst et al. | |
| 2004/0019359 A1 | 1/2004 | Worley et al. | |
| 2004/0059348 A1 * | 3/2004 | Geske et al. | 606/129 |
| 2004/0111080 A1 * | 6/2004 | Harper et al. | 604/892.1 |
| 2004/0122477 A1 | 6/2004 | Whitehurst et al. | |
| 2004/0171986 A1 * | 9/2004 | Tremaglio et al. | 604/116 |
| 2004/0176830 A1 | 9/2004 | Fang | |
| 2004/0210245 A1 | 10/2004 | Erickson et al. | |
| 2004/0243205 A1 | 12/2004 | Keravel et al. | |
| 2005/0015117 A1 | 1/2005 | Gerber | |
| 2005/0027282 A1 | 2/2005 | Schweikert et al. | |
| 2005/0049542 A1 * | 3/2005 | Sigg et al. | 604/20 |
| 2005/0070969 A1 | 3/2005 | Gerber | |
| 2005/0085790 A1 * | 4/2005 | Guest et al. | 604/506 |
| 2005/0154437 A1 * | 7/2005 | Williams | 607/123 |
| 2005/0222628 A1 | 10/2005 | Krakousky | |
| 2005/0246006 A1 | 11/2005 | Daniels | |
| 2005/0256452 A1 * | 11/2005 | DeMarchi et al. | 604/95.04 |
| 2005/0288759 A1 | 12/2005 | Jones et al. | |
| 2006/0025649 A1 | 2/2006 | Smith et al. | |
| 2006/0030899 A1 | 2/2006 | O'Keeffe et al. | |
| 2006/0058575 A1 | 3/2006 | Zaddem et al. | |
| 2006/0122676 A1 | 6/2006 | Ko et al. | |
| 2006/0189940 A1 | 8/2006 | Kirsch | |
| 2006/0217755 A1 | 9/2006 | Eversull et al. | |
| 2006/0270978 A1 * | 11/2006 | Binmoeller et al. | 604/104 |
| 2007/0118196 A1 * | 5/2007 | Rooney et al. | 607/116 |

FOREIGN PATENT DOCUMENTS

| | | |
|---|---|---|
| EP | 0 655 257 | 5/1995 |
| EP | 1 048 271 | 11/2000 |
| EP | 1 360 972 | 11/2003 |
| JP | 2000-271225 | 10/2000 |
| WO | WO 89/01797 | 3/1989 |
| WO | WO 95/28976 | 11/1995 |
| WO | WO 97/30746 | 8/1997 |
| WO | WO 99/30762 | 6/1999 |
| WO | WO 00/76404 | 12/2000 |
| WO | WO 01/02047 | 1/2001 |
| WO | WO 01/89626 | 11/2001 |
| WO | WO 02/34330 | 5/2002 |
| WO | WO 02/068042 | 9/2002 |
| WO | WO 03/026736 | 4/2003 |
| WO | WO 03/047687 | 6/2003 |
| WO | WO 2004/009150 | 1/2004 |
| WO | WO 2004/012613 | 2/2004 |
| WO | WO 2004/012812 | 2/2004 |
| WO | WO 2004/060464 | 7/2004 |

OTHER PUBLICATIONS

Notification of Transmittal of the International Search Report and the Written Opinion for corresponding PCT Application No. PCT/US2006/022494, dated Oct. 20, 2006 (11 pgs.).

Reply to Written Opinion for corresponding PCT Application No. PCT/US2006/022494, dated Apr. 9, 2007 (10 pgs.).

Notification of Transmittal of the International Preliminary Report on Patentability for corresponding PCT Application No. PCT/US2006/022494, dated May 18, 2007 (10 pgs.).

U.S. Appl. No. 11/450,133, filed Jun. 9, 2006, entitled "Combination Therapy Including Peripheral Nerve Field Stimulation."

U.S. Appl. No. 11/450,127, filed Jun. 9, 2006, entitled "Implantable Medical Device with Electrodes on Multiple Housing Surfaces."

U.S. Appl. No. 11/450,144, filed Jun. 9, 2006, entitled "Peripheral Nerve Field Stimulation and Spinal Cord Stimulation."

U.S. Appl. No. 11/450,148, filed Jun. 9, 2006, entitled "Implantable Medical Lead."

U.S. Appl. No. 11/374,852, filed Mar. 14, 2006, entitled "Regional Therapies for Treatment of Pain."

U.S. Appl. No. 11/375,492, filed Mar. 14, 2006, entitled "Regional Therapies for Treatment of Pain."

U.S. Appl. No. 11/374,793, filed Mar. 14, 2006, entitled "Regional Therapies for Treatment of Pain."

Office Action for EP Application No. 06760740.8, mailed Sep. 22, 2008, 2 pgs.

Office Action dated Sep. 8, 2009 for U.S. Appl. No. 11/450,148 (5 pgs.).

Office Action dated Oct. 6, 2009 for U.S. Appl. No. 11/450,127 (7 pgs.).

Responsive Amendment dated Dec. 8, 2009 for U.S. Appl. No. 11/450,148 (8 pgs.).

Responsive Amendment dated Jan. 6, 2010 for U.S. Appl. No. 11/450,127 (9 pgs.).

* cited by examiner

INTRODUCER FOR THERAPY DELIVERY ELEMENTS

This application claims the benefit of U.S. Provisional Application No. 60/689,201, filed Jun. 9, 2005. This application is also a continuation-in-part of each of U.S. application Ser. No. 11/374,852, filed on Mar. 14, 2006, Ser. No. 11/375,492, filed on Mar. 14, 2006, and Ser. No. 11/374,793, filed on Mar. 14, 2006, each of which claims the benefit of U.S. Provisional Application Nos. 60/700,627, filed on Jul. 19, 2005, and 60/761,823, filed on Jan. 25, 2006. The entire content of each of these applications is incorporated herein by reference.

TECHNICAL FIELD

The invention relates to implantable medical devices and, more particularly, to implantation of implantable medical device.

BACKGROUND

Therapy elements such as percutaneous leads and catheters can be implanted through the skin to facilitate the delivery of stimulation therapy or therapeutic agents, e.g., drugs, to patients. Stimulation or therapeutic agents may be used to treat a variety of symptoms or conditions. For example, stimulation or therapeutic agents may be used to treat chronic pain, movement disorders, pelvic floor disorders, Parkinson's disease, spinal cord injury, incontinence, gastroparesis, sexual dysfunction, and a wide variety of other medical conditions.

Percutaneous leads and catheters are often preferred over surgically implanted leads and catheters because percutaneously implanted leads and catheters are implanted in a less invasive manner. For example, in order to implant percutaneous leads for spinal cord stimulation (SCS) an incision is made to ease the introduction of an introducer, such as a percutaneous needle. The needle is inserted through the incision and positioned to access the epidural space. The lead is then inserted through the needle and positioned to a desired location, e.g., within the epidural space. After the lead has been properly positioned, the needle is withdrawn and the lead is connected to a stimulation device. The stimulation device is typically implanted just below the patient's skin.

For many applications, such as epidural implantation of a distal end of a lead for SCS, tunneling of the introducer through a significant amount of tissue is not required. Such applications instead involve use of a separate tunneling device to create a tunnel from an implant site of the stimulation device to the lead. The tunneling device may then be used to pull a proximal end of the lead to the implant site of stimulation device to connection to the stimulation device.

SUMMARY

In general, the invention is directed to an introducer for facilitating implantation of therapy elements into a patient. The introducer has an elongated body that defines a lumen for advancement of a therapy element, such as an implantable medical device (IMD), implantable medical lead, or catheter, to an implant site. The introducer includes a curved portion medially located between substantially straight proximal and distal portions. As an example, the shape of the introducer may allow a clinician to more easily, and without substantially damaging surrounding tissue, find the correct tissue depth and follow that tissue depth to the implant site. For example, the introducer may facilitate implantation of a therapy element within or between desired layers of tissue of the patient.

Typically, introducers that facilitate implantation of therapy elements into a patient are substantially straight over there entire length, or may include a small curvature at or very near their distal end. Such introducers provide access to an implant location, such as an epidural space, with minimal trauma to tissue. However, therapy elements, such as implantable medical devices, electrical leads for stimulation, and catheters for delivering therapeutic agents, may be implanted within a layer of tissue or between layers of tissue and substantially parallel to the skin or a nerve of a patient. For example, peripheral nerve field stimulation (PNFS) may involve implantation of a lead or IMD with housing electrodes within a between desired layers of tissue in a painful region for delivery of stimulation to the painful region. The configuration of conventional introducers may not allow a clinician to advance the introducer though a significant amount of tissue substantially parallel to the skin of a patient or within or between particular tissue layers, without causing substantial trauma to surrounding tissue, or without encountering significant ergonomic difficulty An introducer according the invention may have substantially straight proximal and distal portions and a curved portion located between the proximal and distal portions to facilitate implantation of therapy elements within tissue of a patient. When inserting the introducer into the patient, the curved portion may allow a clinician to more easily find the correct tissue depth with the distal portion and reduce the trauma to surrounding tissue. The substantially straight distal portion may allow the clinician to follow that dermal depth to the implant site, i.e., advance the introducer substantially parallel to the skin of the patient to the implant site.

The substantially straight proximal portion extends through the skin of the patient and provides the clinician a structure to use in guiding the introducer to the implant site and an opening for inserting a therapy element to the implant site. For example, the proximal portion may be attached to or act as a handle to allow the clinician to apply force substantially in the direction of advancement, e.g., in a direction parallel to the distal portion the introducer, with a hand located relatively comfortably above the skin. After inserting the therapy element, the clinician may withdraw the introducer leaving the therapy element implanted substantially parallel the skin of the patient.

The curved portion is located medially between the proximal and distal portions but, depending on the respective lengths of the proximal and distal portions, may be located closer to the end through which the therapy element enters the lumen. Accordingly the length of the distal portion may be greater than or substantially equal to the length of the proximal portion, and may be at least two times the length of the proximal portion. The length of the distal portion may be chosen based on a length of the lead delivering neurostimulation, i.e., the distal end of the lead that carries one or more electrodes, or a distance between a stimulation site for implantation of the distal end of the lead and an implant site for a stimulator. The length of the proximal region may depend on the angle of the curved portion and the depth of the depth of the implant site. The angle of the curved portion, i.e., the angle between the longitudinal axis of the proximal and distal portions, may be selected to facilitate advancing the introducer to the implant site. For example, the angle may be within a range of approximately twenty degrees to approximately sixty degrees.

To insert the introducer, a clinician may make an incision to ease introduction into the patient. A stylet may be inserted into the introducer prior to inserting the introducer into the patient. The stylet may be sized to substantially fill the lumen to prevent coring of tissue during implantation.

The distal end of the stylet may be tapered to an edge or pointed for tissue dissection, and may also enable a clinician to follow a dermal depth the implant site. For example, the distal end of the stylet may allow for tracking a single dermal layer, or between layers by separating the layers during advancement, without damaging tissue above or below the layer. The distal end of the lead stylet may act as a guide that maintains advancement between tissue layers. The clinician may grasp a proximal end of the lead stylet that extends out of the proximal end of the introducer to guide the introducer to the implant site. Alternatively, the clinician may grasp a proximal portion of the introducer or a handle protruding from the proximal portion to guide to introducer to the implant site.

After the introducer is advanced to the implant site, a source may be used to inject or otherwise provide fluid to the implant site proximate to the distal end of the introducer to create a space within the tissue to implant the therapy element. The fluid may be provided via the introducer lumen or outside of the introducer lumen. In this manner, the clinician may create a space within the tissue at the implant site, e.g., by separating tissue layers, while advancing the catheter through the tissue. Delivery of fluid may cause less damage to tissue than using manual devices and methods. Additionally, the fluid may provide support to tissue surrounding the space to prevent the space from collapsing.

A therapy element may be implanted within the space created at the implant site by inserting the therapy element through the introducer. For example, the therapy element may be inserted after fluid is injected to create a space in the tissue. The introducer may be implanted within intra-dermal, deep dermal, or subcutaneous tissue or, alternatively, between different layers of tissue, such as between intra-dermal and deep dermal tissue, or between the deep dermal and subcutaneous tissue. A therapy element may be inserted through the introducer to the implant site to deliver therapy, e.g., neurostimulation or drug therapy, to any one or more of these layers.

The therapy element may comprise an implantable medical device, lead, or catheter. An implantable medical device may comprise any IMD carrying one or more electrodes on its housing for delivery of stimulation to tissue proximate to the implant site. An implantable medical lead may comprise any electrical lead carrying electrodes on a distal end and including a proximal end that couples to an internal or external pulse generator. Implantable medical leads may include leads carrying ring electrodes, paddle leads carrying pad electrodes, cuff electrodes, and the like. An implantable catheter may be coupled to a drug pump for delivering one or more drugs to a patient. The introducer may have a substantially round or rectangular shape sized to pass a lead carrying ring electrodes or a paddle lead, although any shape is possible to facilitate implantation of a therapy element.

A vacuum source may evacuate fluid from the space, e.g., via the lumen, after the therapy element has been implanted. The vacuum source and fluid source may, in some embodiments, comprise a common pump.

In one embodiment, the invention is directed to a device to facilitate implantation of a therapy element into a patient comprising an elongated body having proximal and a distal end for insertion into tissue of the patient. The elongated body defines a lumen sized for insertion of the therapy element from the proximal end to the distal end through the lumen. The elongated body comprises a substantially straight proximal portion, a substantially straight distal portion, and a curved portion located between the proximal portion and the distal portion. A length of the distal portion is greater than or approximately equal to a length of the proximal portion.

In another embodiment, the invention is directed to a kit to facilitate implantation of therapy elements into a patient comprising a therapy element, and an introducer comprising an elongated body having proximal and a distal end for insertion into tissue of the patient. The elongated body defines a lumen sized for advancement of the therapy element from the proximal end to the distal end through the lumen. The elongated body comprises a substantially straight proximal portion, a substantially straight distal portion, and a curved portion located between the proximal portion and the distal portion. A length of the distal portion is greater than or approximately equal to a length of the proximal portion.

In another embodiment, the invention is directed to a method comprising inserting an introducer into a patient, the introducer comprising an elongated body having proximal and a distal end for insertion into tissue of the patient, the elongated body defining a lumen, advancing the distal end of the elongated body through tissue of the patient to a position within the patient proximate to a therapy delivery site, and advancing a therapy element from the proximal end of the elongated body to the distal end of the elongated body through the lumen to implant the therapy element at the therapy delivery site. The elongated body comprises a substantially straight proximal portion, a substantially straight distal portion, and a curved portion located between the proximal portion and the distal portion. A length of the distal portion is greater than or approximately equal to a length of the proximal portion.

Various embodiments of the invention may provide one or more advantages. For example, the shape of the introducer, i.e., the curved portion located medially between substantially straight proximal and distal portions, may allow a clinician to more easily, and without substantially damaging surrounding tissue, implant a therapy element within or between layer of tissue of the patient and, more particularly, find the correct tissue depth and follow that depth to the implant site. The introducer may also provide ergonomic advantages by providing a handle or handle like structure external to the patient for application of force in the direction of advancement of the distal portion of the introducer through tissue. Further, an edge or point provided by a stylet may provide guidance when advancing the distal portion of the introducer through tissue, e.g., may separate layers of tissue and maintain the distal portion between the layers during advancement. Delivery of fluid to an implant site proximate to the distal end of the introducer may provide a space for advancement of a therapy element from the distal end into the implant site. Additionally, the fluid may provide support to tissue surrounding the space to prevent the space from collapsing.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
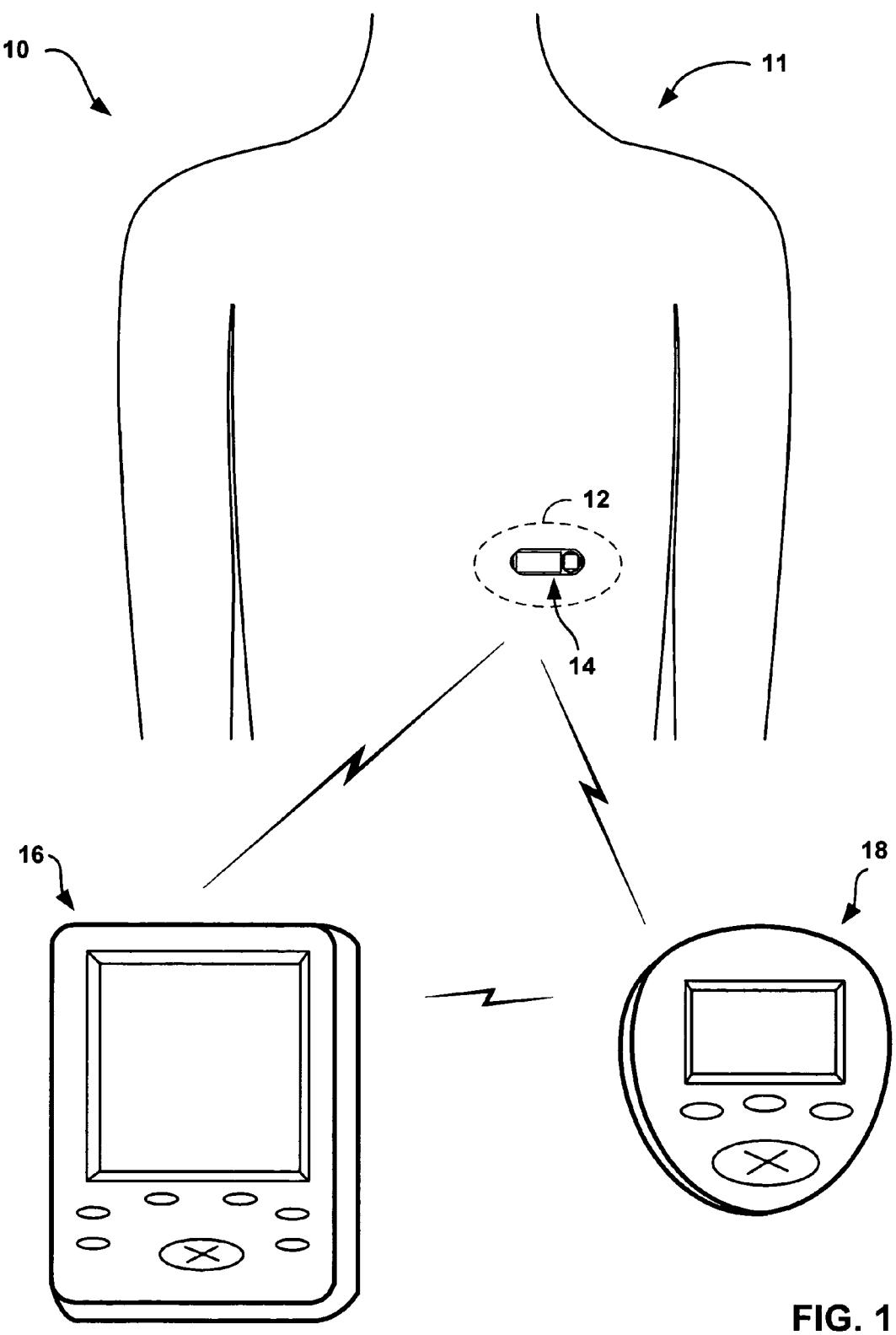
FIGS. 1 and 2 are conceptual diagrams illustrating example systems that include therapy elements implanted within a patient.
Figure 2:
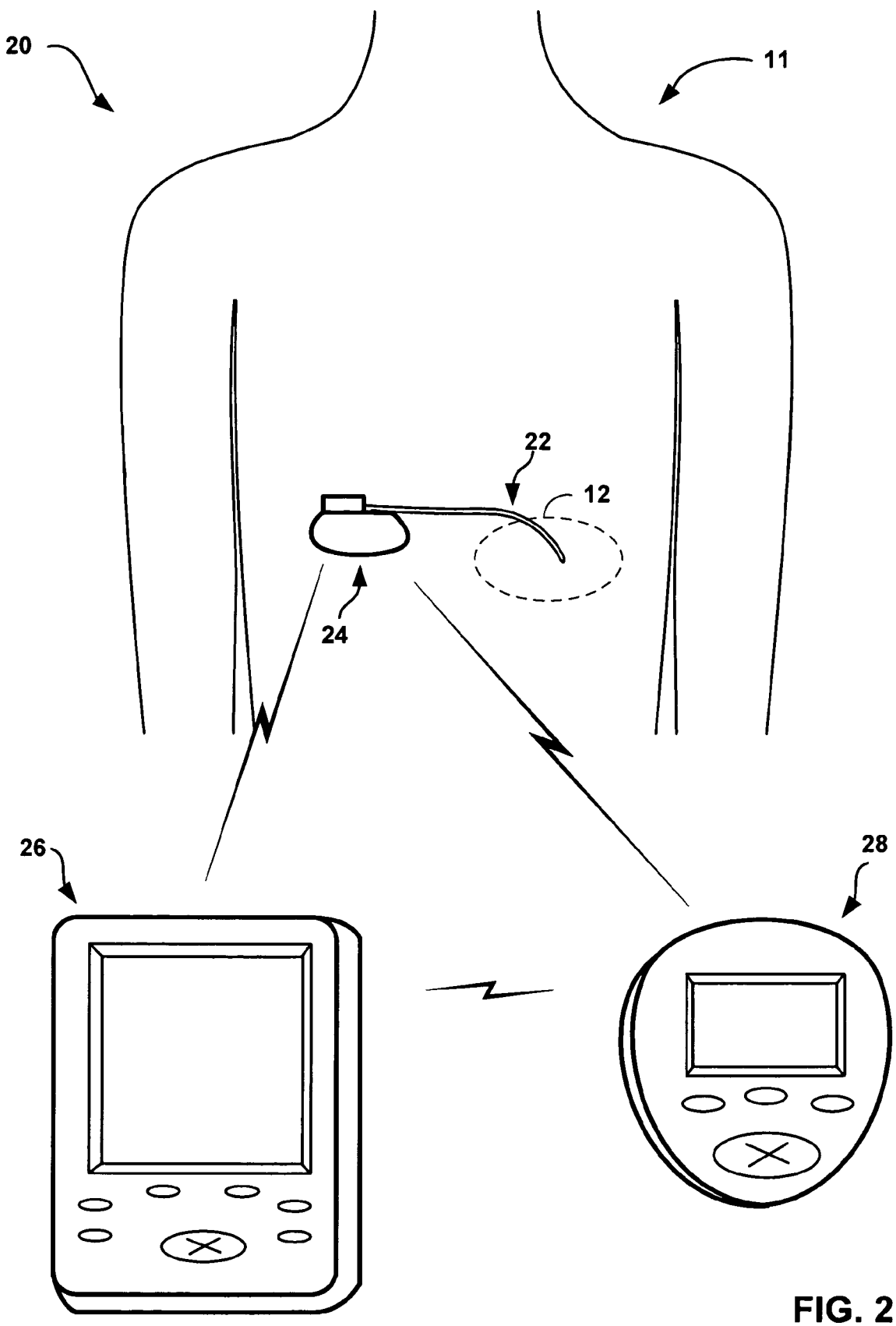

FIGS. 1 and 2 are conceptual diagrams illustrating respective example systems 10 and 20 that include therapy elements implanted within a patient 11. In particular, FIG. 1 illustrates an implantable medical device (IMD) 14 implanted within patient 11 to deliver stimulation. FIG. 2 illustrates an implantable medical lead 22, referred to herein as lead 22, coupled to an implantable pulse generator (IMD) 24 to deliver stimulation. As will be described in greater detail below, an introducer in accordance with the invention may facilitate percutaneous implantation of therapy elements, such as, but not limited to, IMD 14 and lead 22, into patient 11. For example, the introducer may facilitate placement of the therapy element at a particular tissue and advancement of the introducer through tissue substantially at that depth, e.g. substantially parallel to the skin surface of a patient 11

With respect to FIGS. 1 and 2, IMD 14 and lead 22 may be implanted using an introducer in accordance with the invention within or between intra-dermal, deep dermal, or subcutaneous tissue layers. In the illustrated example, IMD 14 and lead 22 deliver peripheral nerve field stimulation (PNFS) to any one or more tissue layers within a region 12 in which patient 11 experiences or perceives pain to ameliorate the pain perceived by patient 11. Region 12 is shown in FIGS. 1 and 2 as an axial region of the lower back of patient 11, but the invention is not limited as such. Rather IMD 14 and lead 22 may be implanted in any region, localized area or dermatome where patient 11 experiences pain.

As examples, IMD 14 and lead 22 may be implanted within various regions of the back, the back of the head, above the eyebrow, over the eye, under the eye, on the chest or in the pelvic region. An introducer according to the invention may be user to facilitate implantation of IMD 14 or lead 22 at any of these locations. IMD 14 and lead 14 may deliver PNFS to, for example, treat failed back syndrome (FBS), cervical pain (shoulder and neck pain), facial pain, headaches supra-orbital pain, inguinal and pelvic pain, chest and intercoastal pain, mixed pain (nociceptive and neuropathic), visceral pain, neuralgia, perineal pain, phantom limb pain, or arthritis.

IMD 14 and lead 22, however, are not limited to embodiments in which IMD 14 and lead 22 deliver PNFS or are implanted within such regions. Rather, IMD 14 and lead 22 may be implanted within any region of the body to provide any of a variety of therapies. For example, IMD 14 and lead 22 may be implanted within the limbs to, for example, provide functional electrical stimulation. As another example, IMD 14 and lead 22 may be implanted within or proximate to the gastrointestinal tract and deliver electrical stimulation to, for example treat gastoparises or other gastric motility disorders. In another example, IMD 14 and lead 22 may be implanted within or proximate to the sacral nerves or pelvic floor and deliver electrical stimulation to, for example, treat incontinence or sexual dysfunction. An introducer according to the invention may also be user to facilitate implantation of IMD 14 or lead 22 at any of these locations.

In the illustrated examples of FIGS. 1 and 2, respective systems 10 and 20 include IMD 14 and lead 22 implanted within a region 12 in which patient 11 experiences pain. IMD 14 may include, for example, a housing (not shown in FIG. 1) that contains internal components, such as control electronics, stimulation generation circuitry, communication circuitry, and a power source. IMD 14 also includes one or more electrodes (not shown in FIG. 1) positioned on one or more surfaces of the housing. The stimulation generation circuitry within IMD 14 may comprise pulse generation circuitry and IMD 14 may deliver stimulation in the form of electrical pulses. IMD 14 may have any shape or size, but preferably may have a miniaturized form factor to facilitate percutaneous implantation within patient 11 using an introducer in accordance with the invention.

Lead 22 of FIG. 2, may include a distal end that carries one or more electrodes (not shown in FIG. 2) and a proximal end that couples to implantable pulse generator (IPG) 24. IPG 24 may contain stimulation generation circuitry, communication circuitry, and a power source and, similar to IMD 14, may deliver stimulation in the form of electrical pulses. Lead 22 may, for example, comprise a substantially cylindrical lead carrying ring electrodes, a paddle lead carrying a linear or two-dimensional array of pad electrodes on one or more surfaces of the lead, a lead carrying cuff electrodes, or any other lead known in the medical device arts. As illustrated in FIG. 1, systems 10 and 20 may include corresponding external programmers 16 and 18 and 26 and 28, which may respectively be used by a clinician and patient 11 to communicate with IMD 14, e.g., via wireless telemetry, for programming and adjustment of therapy using any techniques known in the medical device arts.

Figure 3:
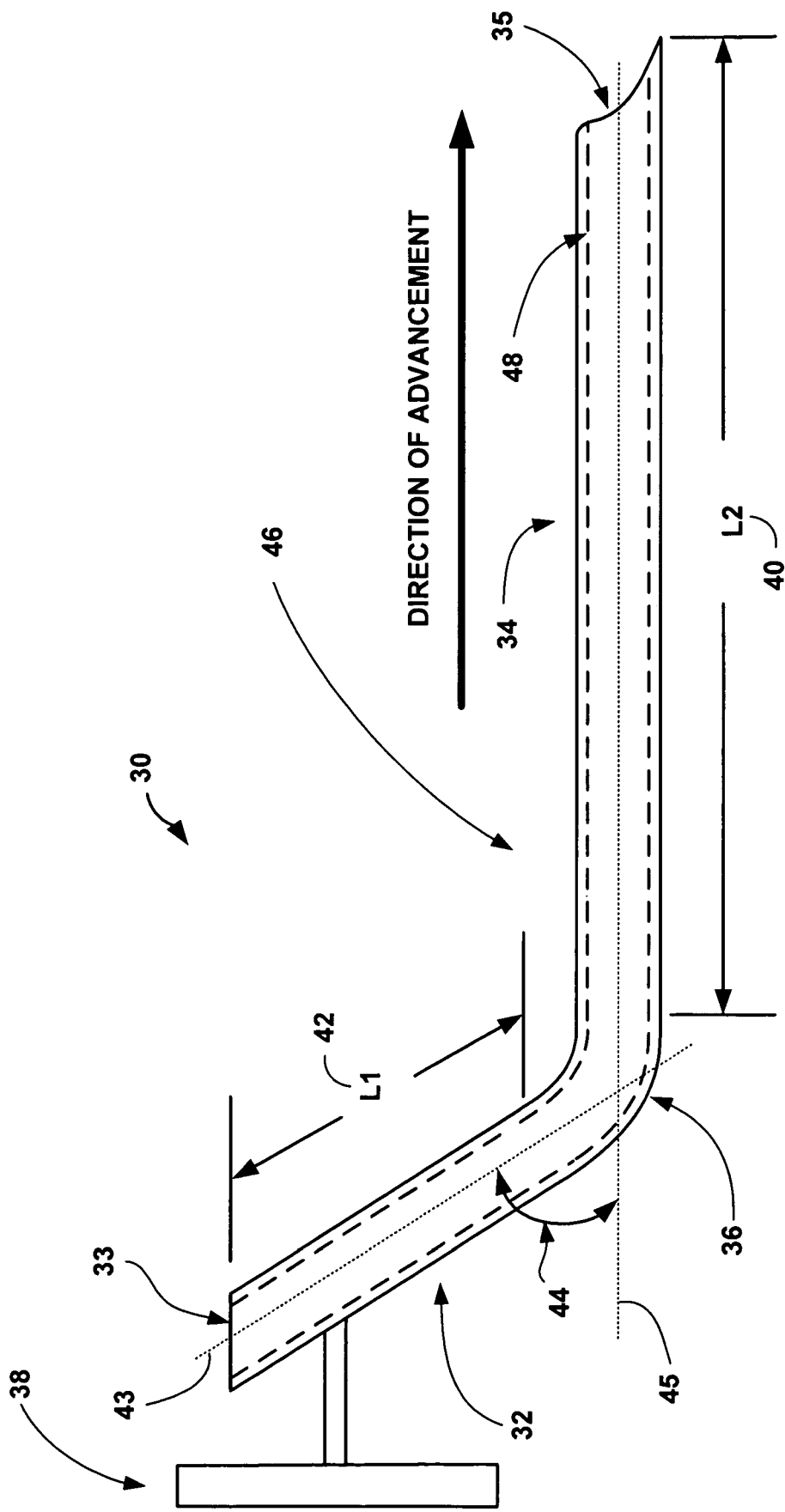
FIG. 3 is a diagram illustrating a side view of an introducer to facilitate implantation of therapy elements into a patient.

FIG. 3 is a schematic diagram illustrating a side view of an introducer 30 to facilitate implantation of therapy elements into a patient. Introducer 30 may, for example, be used to facilitate implantation of IMD 14 (FIG. 1) and lead 22 (FIG. 2) within or between selected tissue layers of painful region 12 of patient 11, but not limited to such applications. Introducer 30 may facilitate implantation of a therapy element within a layer of tissue or between layers of tissue and substantially parallel to the skin of the patient. During implantation, introducer 30 may allow a clinician to more easily find and follow the correct tissue depth to the implant site. Introducer 30 may also cause less damage to tissue when implanting a therapy element than would be possible using a typical introducer, i.e., an introducer that is substantially straight over its entire length, or a surgical procedure.

As shown in the illustrated example of FIG. 3, introducer 30 includes an elongated body 46 that defines a lumen 48 sized to for advancement of a therapy element, such as an IMD, implantable medical lead, or a catheter, from a proximal end 33 of body 46 to a distal end 35 of body 46 through lumen 48. Lumen 48 may have a circular, oval, square, or rectangular shape, although any shape is possible, and may be sized to accommodate any therapy element.

Elongated body 46 includes a substantially straight proximal portion 32, a substantially straight distal portion 34, and a curved portion 36. Curved portion 36 is medially located between proximal and distal portions 32, 34. In particular, curved portion 36 is referred to herein as being "medially located" between proximal and distal portions 32, 34 in the sense that curved portion 36 is located between proximal and distal portions 32, 34. As shown in FIG. 3, curved portion 36 may be located closer to proximal end 33 than distal end 35. Accordingly, the length 40 of distal portion 34 is greater than the length 42 of proximal portion 32.

In some embodiments, length 40 of distal portion 34 may be greater than or approximately equal to length 42 or proximal portion 32. As an example, length 40 may be at least approximately 1.5 times that of length 42. As another example, length, 40 may be approximately twice that of length 42, or greater than twice that of length 42, such as three times length 42. Thus, the depiction of FIG. 3 is merely exemplary and should not be considered limiting of the invention as broadly described in this disclosure.

The length of distal and proximal portions 32, 34 may be determined by implantation parameters. For example, the length of distal portion 34 may be determined by the length of the lead (not shown) delivering neurostimulation. The number of electrodes and spacing between the electrodes, in this case, may determine the length of the proximal portion. The number of electrodes and spacing between electrodes may be related to the region of pain experienced by the patient or the stimulation site. In other words, if a patient experiences pain over a large region or if the stimulation site is large, stimulation may be delivered over a larger area and require a lead with a greater number of electrodes. For example, the length of a lead that delivers PNFS may be determined by the size of the region of pain experienced by the patient. In contrast, the length of a lead that delivers stimulation to a nerve upstream of the pain experienced by the patient, may be determined by the length of the stimulation site along the nerve.

The length of proximal portion 32 may, however, depend on the angle 44 of curved portion 36 and the depth of the implant site. In general, the length of proximal portion 32 may be such that at least a portion of proximal portion 32 extends through the skin of the patient when introducer 30 is fully inserted, i.e., inserted to the implant site. A clinician may grasp this portion of proximal portion 32 to manipulate introducer 30 and insert a therapy element into the patient through introducer 30. In the illustrated example of FIG. 3, introducer 30 includes a handle 38 protruding from proximal portion 32 which a clinician may grasp to assist in manipulating introducer 30 during implantation.

As shown in FIG. 3, angle 44 between a longitudinal axis 45 of distal portion 34 and a longitudinal axis 43 of proximal portion 32. The angle 44 of curved portion 36 may be selected to facilitate advancing introducer 30 to the implant site. In general, angle 44 may be larger for applications requiring a shallower implant site, i.e., an implant site closer to the surface of the skin, and smaller for applications requiring a deeper implant site. As an example, angle 44 may be within a range of approximately twenty degrees to approximately sixty degrees. However, the invention is not limited as such and an introducer in accordance with the invention may include a curved portion having an angle greater or lesser than the limits of this exemplary range. Thus, FIG. 3 is merely exemplary and should not be considered limiting of the invention as broadly described in this disclosure.

Introducer 30 may be made of any material suitable for facilitating implantation of a therapy element. For example, introducer 30 may be made from stainless steel, titanium, and/or plastic, or other biocompatible materials. Introducer 30 may be rigid so that resistance resulting from pushing introducer 30 through tissue does not cause introducer 30 to distort from its original shape. In some embodiments, proximal portion 32, distal portion 34, and curved portion 36 may all be formed of a rigid material. In other words, elongated body 46 of introducer 30 may be preformed and completely rigid. However, in other embodiments, proximal and distal portions 32, 34 may be formed from a rigid material and curved portion 36 may be formed of a semi-rigid material that allows curved portion 36 to flex a small amount. For example, curved portion 36 may flex a small amount such that angle 44 of curved portion 36 may vary as the clinician exerts force on proximal portion 32 during implantation. Flexing of curved portion 36 may allow the clinician to more easily find and follow the correct dermal depth to the implant site as well as cause less damage to tissue.

Figure 4:
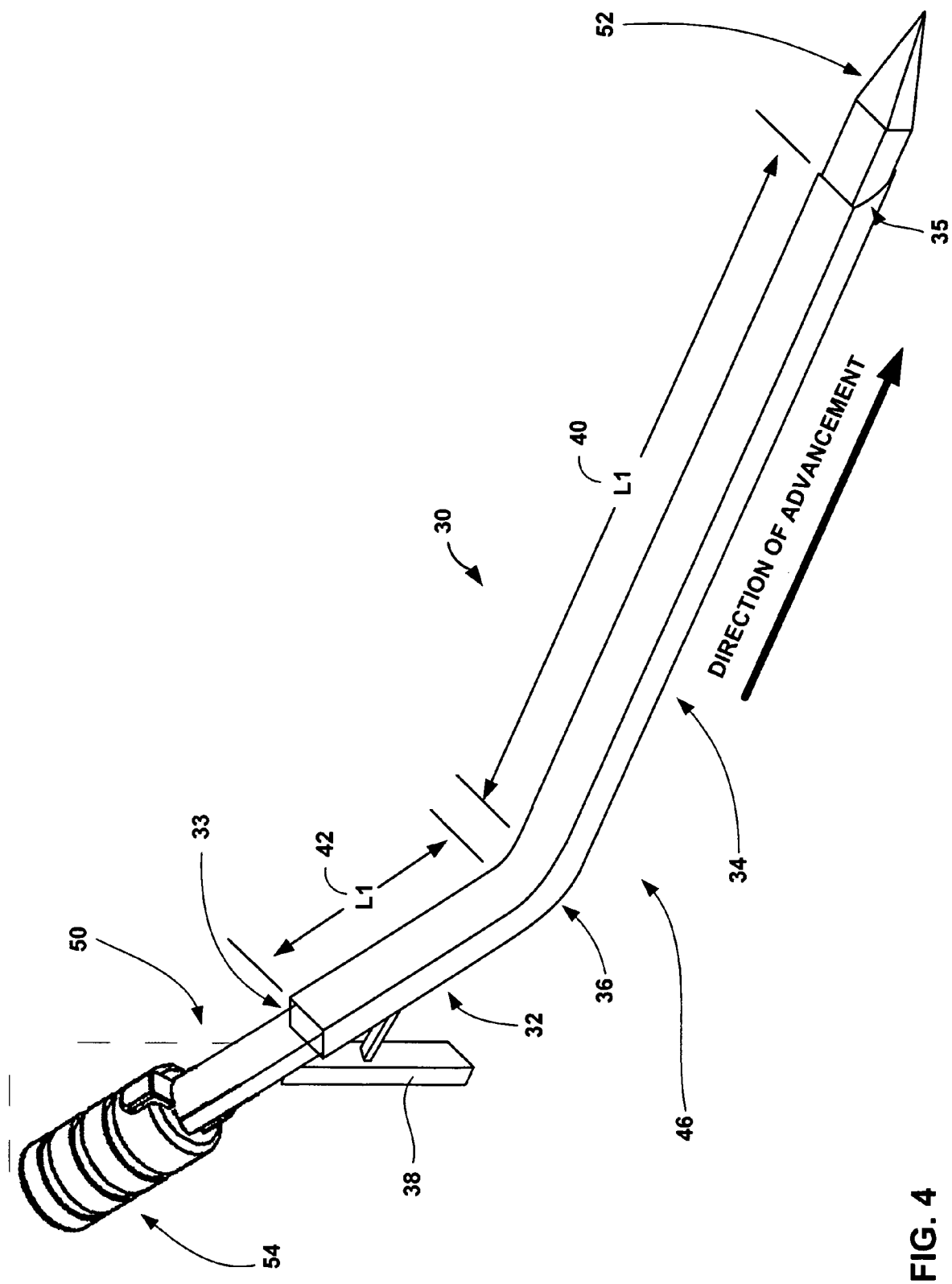
FIG. 4 is schematic diagram illustrating a perspective view of the introducer and a lead stylet that facilitates tissue dissection.

FIG. 4 is schematic diagram illustrating an introducer 30 and a stylet 50 that facilitates tissue dissection. In the interest of clarity, every reference numeral associated with introducer 30 is not included in FIG. 4. In particular, longitudinal axis 43 of proximal portion 32, length 40 of proximal portion 32, longitudinal axis 45 of distal portion 34, length 34 of distal portion 34, lumen 48, and angle 44 are omitted from FIG. 4. However, these reference numerals are used in the description of FIG. 3 and throughout this disclosure.

FIG. 4 illustrates a three-dimensional representation of introducer 30 with stylet 50 inserted within introducer 30. As shown in FIG. 4, introducer 30 has a substantially rectangular or square cross-section. On each side of the rectangular cross section of introducer 30, introducer 30 includes continuous and smooth external surfaces that extend over proximal portion 32, distal portion 34 and curved portion 36. Stylet 50 may be inserted within introducer as shown in FIG. 4 during the implantation process to prevent coring of tissue and assist in tissue dissection, as will be described in greater detail below. More specifically, stylet 50 may be inserted within introducer 30 prior to advancement of introducer 30 through the skin of the patient towards the implantation site. FIG. 4 includes a labeled arrow to provide a reference for the direction in which introducer is advanced within the patient.

During implantation of introducer 30, stylet 50 is inserted within introducer 30 as shown in FIG. 4, i.e., with proximal portion 54 extending through proximal end 33 and distal portion 52 extending through distal end 35. As shown in FIG. 4, stylet 50 may be sized to substantially fill lumen 48 (not shown in FIG. 4). Stylet 50 may have a substantially flat rectangular shape as shown in FIG. 4, but any shape and size is possible.

When inserted in introducer 30, proximal portion 54 may extend through proximal end 33 a distance that allows a clinician to grasp proximal portion 54 and use proximal portion 54 during implantation to manipulate or guide introducer to the implant site. A clinician may, in a similar fashion, grasp and use handle 38 to guide introducer to the implant site. However, in such embodiments, proximal portion 54 may still extend through the proximal end 33 of introducer to allow a clinician to withdraw stylet 50 from introducer 30 when introducer has been advanced to the implant site.

Distal portion 52 may protrude a distance through distal end 35 such that distal end dissects tissue, instead of or in addition to distal end 35 of introducer 30, as introducer 30 is advanced toward the implant site. Distal portion 52 of stylet 50 may be tapered to a substantially flat edge or a point to dissect tissue with minimal damage and to enable a clinician to more easily follow a dermal depth as introducer 30 is advanced toward the implant site. The shape of distal portion 52 may assist a clinician in advancing introducer 30 within or between dermal layers without significantly damaging tissue or other layers above or below by providing a substantially planar guide. Distal portion 52 may have any of a variety of rounded or pointed shapes. Further, in some embodiments, distal end 52 may rotate to "drill" into and excavate tissue as introducer 30 is advanced to an implantation site.

Stylet 50 may be made of any material suitable for facilitating implantation of a therapy element. Stylet 50 may be made of a rigid material so that stylet 50 does not distort from its original shape as it dissects tissue. For example, introducer 30 may be made from stainless steel and/or polyvinylchloride, or other biocompatible materials.

Figure 5:
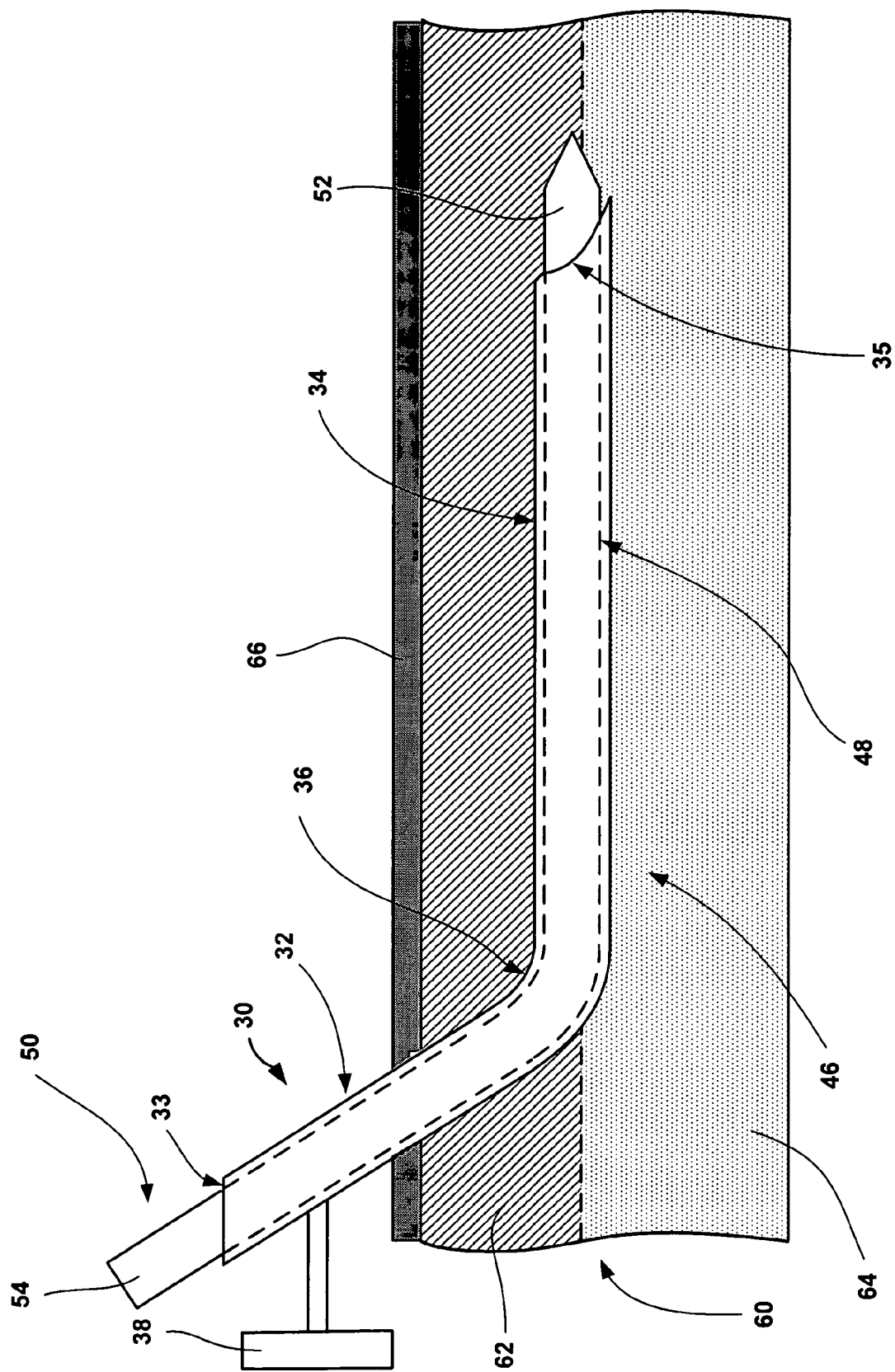
FIG. 5 is a conceptual diagram illustrating a side view of the introducer implanted between layers of tissue.

FIG. 5 is a cross section illustrating introducer 30 implanted between two layers of tissue 60. In the interest of clarity, every reference numeral associated with introducer 30 is not included in FIG. 5. In particular, longitudinal axis 43 of proximal portion 32, length 42 of proximal portion 32, longitudinal axis 45 of distal portion 34, length 40 of distal portion 34, and angle 44 are omitted from FIG. 5. However, these reference numerals are used in the description of FIG. 3 and throughout this disclosure.

In particular, FIG. 5 illustrates introducer 30 inserted within tissue 60 and, more particularly, between tissue layers 62 and 64, such that distal portion 34 is substantially parallel to the skin of the patient. As previously described, introducer 30 may be implanted within intra-dermal, deep dermal, or subcutaneous tissue or, alternatively, between different layers of tissue, such as between intra-dermal and deep dermal tissue, or between deep dermal and subcutaneous tissue. In the illustrated example of FIG. 5, tissue layer 62 is located shallower or superior to tissue layer 64, i.e., closer to the surface of the skin of the patient. Tissue layer 66 may represent a layer of tissue including the intra-dermal layer. Accordingly, tissue layer 62 may represent deep dermal tissue and tissue layer 64 may represent subcutaneous tissue.

As previously described, proximal portion 32 of introducer 30 extends through the proximal portion 54 of stylet 50 through tissue layer 66, i.e., the skin of the patient. In addition, distal portion 34 is substantially parallel to tissue layer 66, i.e., the skin of the patient. Further, distal portion 34 and distal end 35 may be located substantially between layers 62 and 64, by advancement between the layers.

Figure 6:
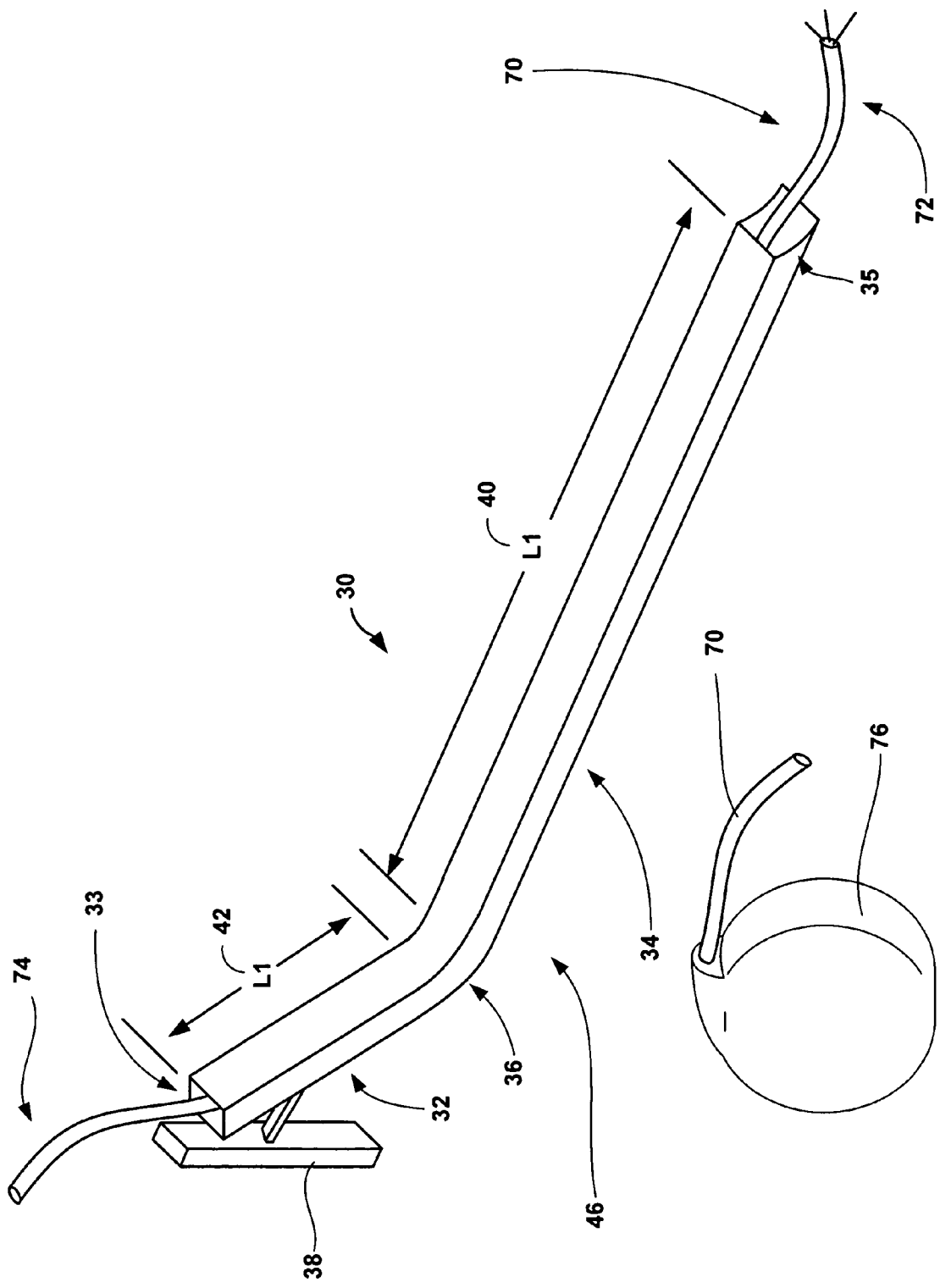
FIG. 6 is a schematic diagram illustrating the introducer and a fluid pump for creating a space within tissue.

FIG. 6 is a schematic diagram illustrating introducer 30 and a fluid source 76 for creating a space within tissue to implant a therapy element. FIG. 6 does not include every reference numeral associated with introducer 30 in order to avoid confusion. In particular, longitudinal axis 43 of proximal portion 32, length 40 of proximal portion 32, longitudinal axis 45 of distal portion 34, length 34 of distal portion 34, lumen 48, and angle 44 are omitted from FIG. 6. However, these reference numerals are used in the description of FIG. 6 and throughout this disclosure.

In some embodiments, fluid source 76, which may include a pump, may inject fluid at the implant site to create space for implanting a therapy element within a patient. In such embodiments, the clinician may first advance introducer 30 to the implant site as previously described, for example, using stylet 50 to prevent tissue coring and assist in tissue dissection. When introducer is implanted at the implant site, stylet 50 may be withdrawn and catheter 70 may be inserted as shown in FIG. 6. For example, catheter 70 may be inserted such that a distal portion 72 protrudes through distal end 35 of introducer 30 and a proximal portion 74 extends through the proximal end of introducer 30 to couple catheter 70 to fluid source 76.

Fluid source 76 may include a housing, a power supply carried in the housing, a reservoir that contains saline or other biocompatible fluid, a pump that pumps fluid from the reservoir to the implant site via catheter 70, and electronics coupled to the battery and the pump. Fluid source 76 may inject fluid via catheter 70 in an automated manner, or as controlled by a user.

In this manner, fluid source 76 may be used to automatically inject fluid to create a space within the tissue by delivering fluid through introducer 30 via catheter 70. However, in other embodiments, fluid may be delivered directly through lumen 48, e.g., by coupling fluid source 76 to proximal end 33 of elongated body 46. In yet other embodiments, fluid source 76 may inject fluid to create space within the tissue by delivering fluid outside introducer 30. In this case, catheter 70 may be inserted to the implant site independent of introducer 30 and may continuously inject fluid as a therapy element is implanted through introducer 30 as described in detail below. Further, the invention is not limited to embodiments that include a non-manual pump. In other embodiments, a syringe, bulb-syringe, plunger or the like, with or without catheter 70, may be used by a clinician to manually deliver fluid to the implant site.

In addition, a pump of fluid source 76 operated in reverse or another vacuum source may be used to evacuate fluid and loose tissue from the implant site. In this case, the fluid and loose tissue may be evacuated after a therapy element has been inserted through introducer 30.

Figure 7:
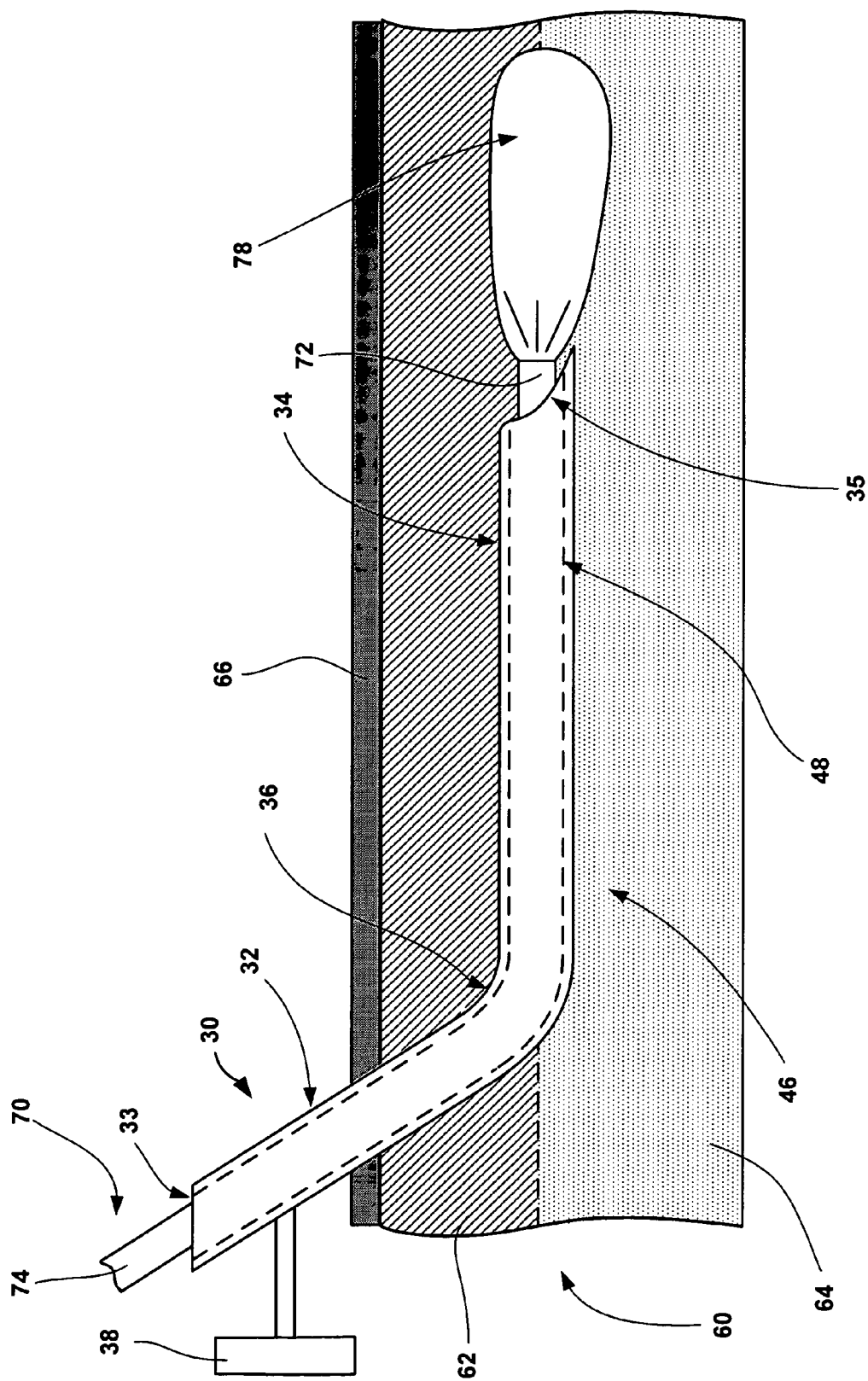
FIG. 7 is a conceptual diagram illustrating the fluid injection device inserted in the introducer implanted within the patient and a space created between layers of tissue.

FIG. 7 is a cross section illustrating introducer 30 implanted between two layers of tissue 60 and a space 78 within tissue 60 for implanting a therapy element. In the interest of clarity, every reference numeral associated with introducer 30 is not included in FIG. 7. In particular, longitudinal axis 43 of proximal portion 32, length 42 of proximal portion 32, longitudinal axis 45 of distal portion 34, length 40 of distal portion 34, and angle 44 are omitted from FIG. 7. However, these reference numerals are used in the description of FIG. 7 and throughout this disclosure. Fluid source 76 is also not shown in FIG. 7, although it is understood that proximal portion 74 of catheter 70 is coupled to fluid source 76. As shown in FIG. 7, catheter 70 injects fluid to create space 78 within tissue 60 and, more particularly between tissue layers 62 and 64, for implanting a therapy element, e.g., the injected fluid separates the layers.

FIG. 8A is a schematic diagram illustrating introducer 30 that facilitates implantation of lead 80. FIG. 8A does not include every reference numeral associated with introducer 30 in order to avoid confusion. In particular, longitudinal axis 43 of proximal portion 32, longitudinal axis 45 of distal portion 34, lumen 48, and angle 44 are omitted from FIG. 8A.

However, these reference numerals are used in the description of FIG. 8A and throughout this disclosure.

Figure 8:
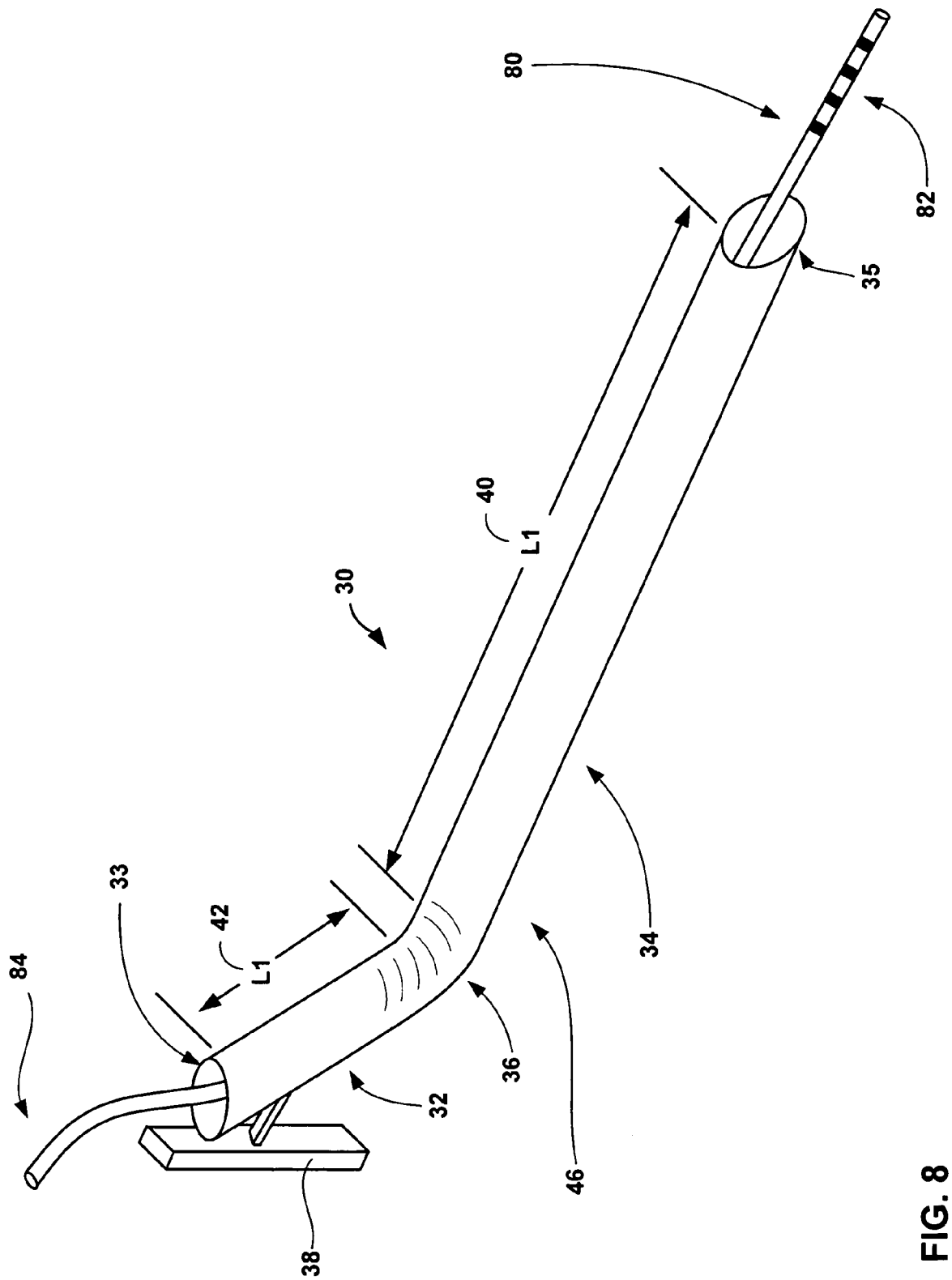
FIG. 8 is a schematic diagram illustrating an introducer to facilitate implantation of an electrical stimulation lead into a patient.

In particular, FIG. 8 illustrates lead 80 inserted into introducer 30. Lead 80 may be inserted into introducer 30 after introducer has been advanced to the implant site within the patient, as previously described. As shown in FIG. 8, lead 80 may comprise an implantable medical lead carrying ring electrodes 82 on its distal end. Although four ring electrodes are depicted in FIG. 8, lead 80 may carry a greater or lesser number of electrodes. For example, lead 80 may carry 2, 8, 16, 32, or any other number of ring electrodes. Lead 80 may be coupled to an internal or external pulse generator via proximal portion 84. The pulse generator may deliver stimulation in the form of electrical pulses to the patient via electrodes 82.

Figure 9:
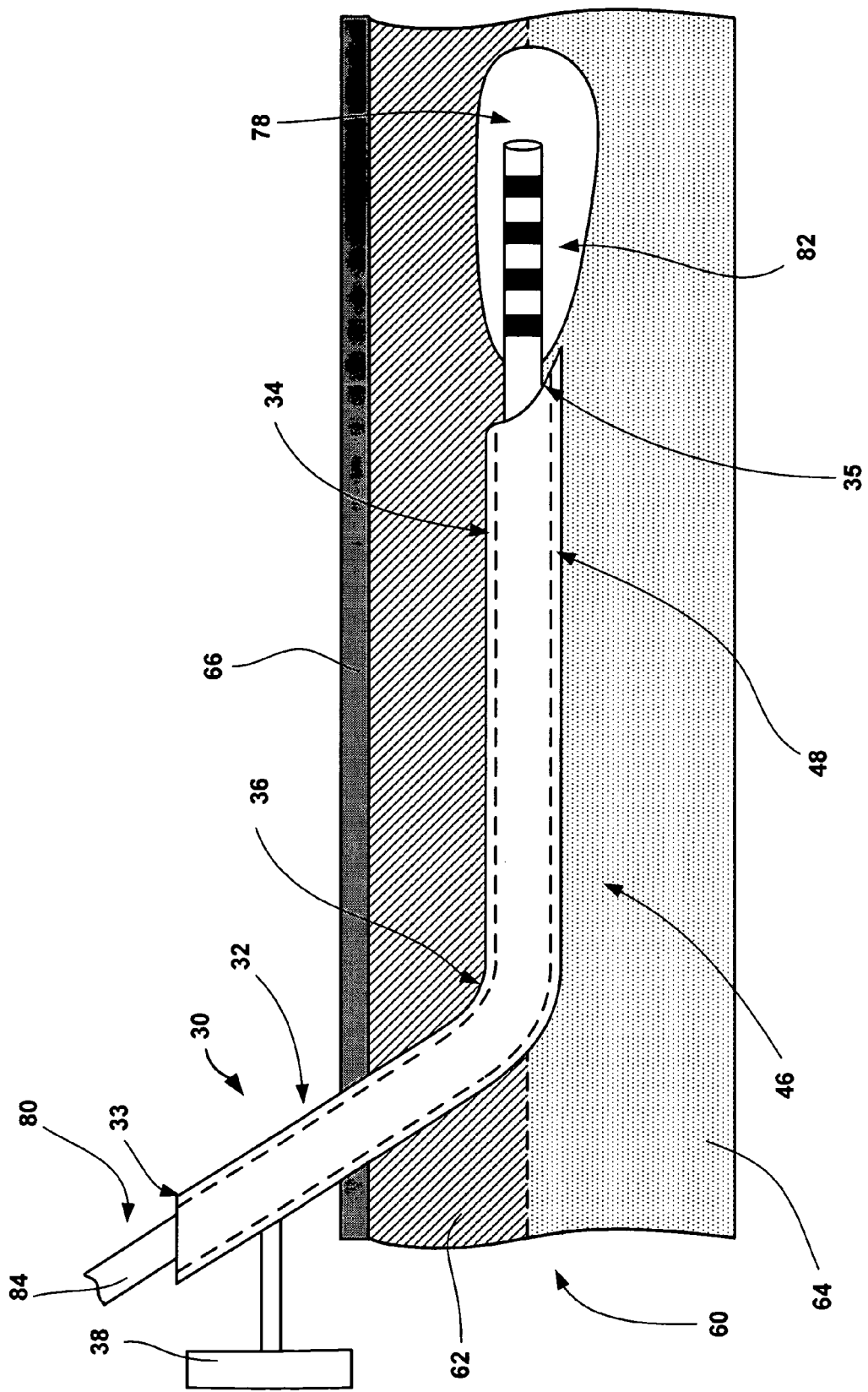
FIG. 9 is a conceptual diagram illustrating the lead inserted through the introducer and implanted into the patient.

FIG. 9 is a cross section illustrating introducer 30 implanted between two layers of tissue 60 and lead 80 implanted within space 78 through introducer 30. To avoid confusion, every reference numeral associated with introducer 30 is not included in FIG. 9. In particular, longitudinal axis 43 of proximal portion 32, length 42 of proximal portion 32, longitudinal axis 45 of distal portion 34, length 40 of distal portion 34, and angle 44 are omitted from FIG. 5. However, these reference numerals are used in the description of FIG. 9 and throughout this disclosure.

In FIG. 9, lead 80 is implanted within space 78 between tissue layers 62 and 64. After lead 80 has been implanted as shown in FIG. 9, introducer 30 may be removed leaving lead implanted between layers 62 and 64 and substantially parallel to the surface of the skin 66 of the patient. As a result, lead 80 may stimulate tissue and/or nerves in tissue layers 62 and 64.

Figure 10:
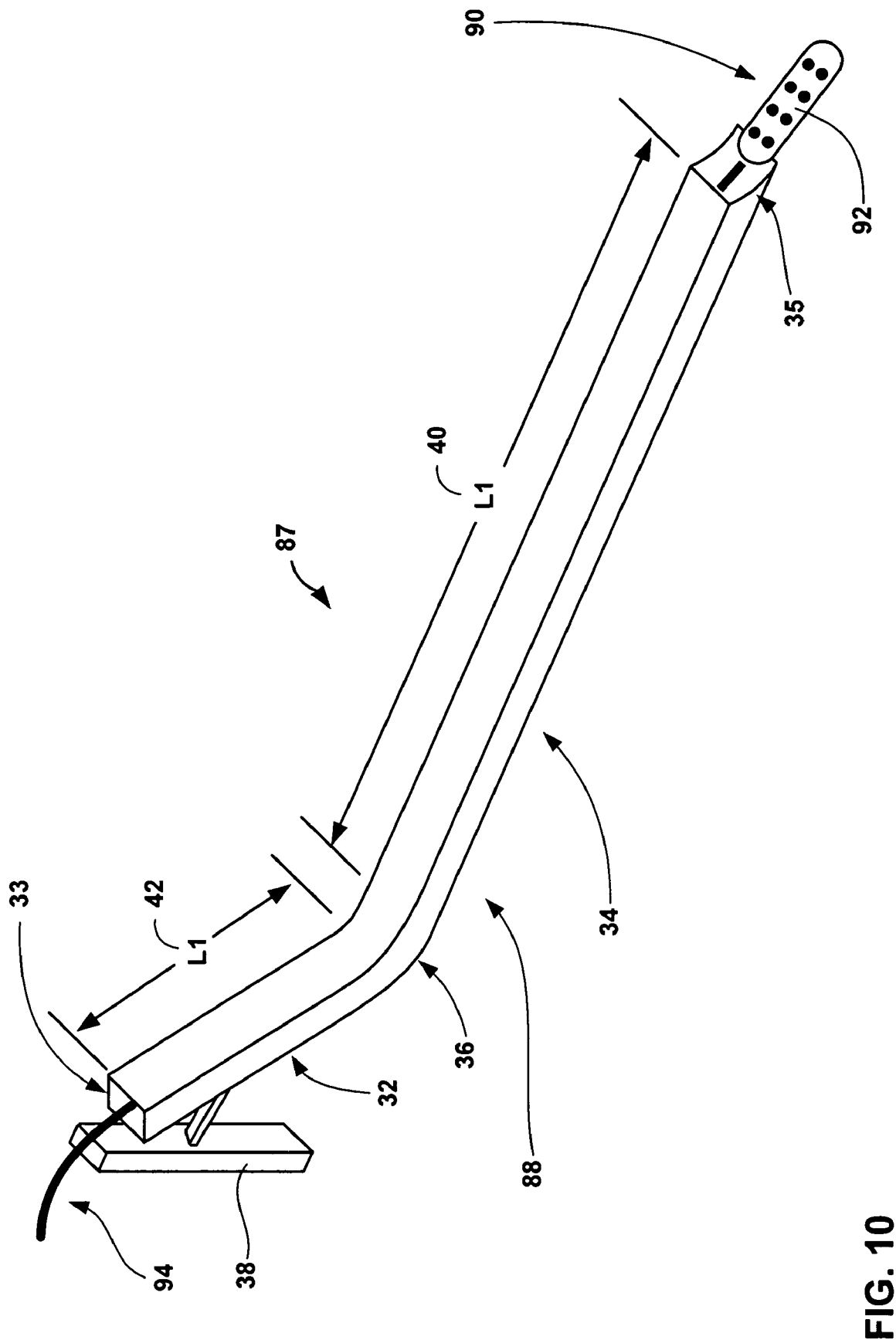
FIG. 10 is a schematic diagram illustrating an introducer to facilitate implantation of another type of electrical stimulation lead into a patient.

FIG. 10 is a schematic diagram illustrating another introducer 88 that facilitates implantation of paddle lead 90. FIG. 10 includes similar references numbers for the features that are similar to introducer 30 of FIG. 3, but does not include every reference numeral associated with introducer 30 in order to avoid confusion. In particular, longitudinal axis 43 of proximal portion 32, longitudinal axis 45 of distal portion 34, and angle 44 are omitted from FIG. 10. However, these reference numerals are used in the description of FIG. 10 and throughout this disclosure.

Further, as shown in FIG. 10, introducer has a substantially rectangular or square cross-section to accommodate the similar cross-section of paddle lead 90. rather than the substantially circular or ellipsoid cross-section illustrated with respect to introducer 30 and FIG. 8. In the illustrated embodiment, both the elongated body 88 and lumen 89 (FIG. 12) of introducer 87 have substantially rectangular cross-sections. In other embodiments, the lumen alone may have a substantially rectangular cross-section. The invention is not limited to rectangular or ellipsoid cross-sections, and the elongated body and/or lumen of an introducer may have any cross-section to accommodate therapy delivery elements with any cross-sectional shape.

FIG. 10 illustrates paddle lead 90 inserted into introducer 87. Paddle lead 90 may be inserted into introducer 88, which may be sized to accommodate paddle lead 90, after introducer has been advanced to the implant site within the patient as previously described. As shown in FIG. 10, lead 90 may comprise an implantable medical lead carrying a two dimensional array of electrodes 92. However, FIG. 10 is merely exemplary and should not be considered limiting of the invention as broadly described in this disclosure. Rather, paddle lead 90 may any number of electrodes arranged in a linear array or a two dimensional array on one or more of its surfaces. Paddle lead 90 may be coupled to an internal or external pulse generator via proximal portion 94. The pulse generator may deliver stimulation in the form of electrical pulses to the patient via electrodes 92.

Figure 11A:
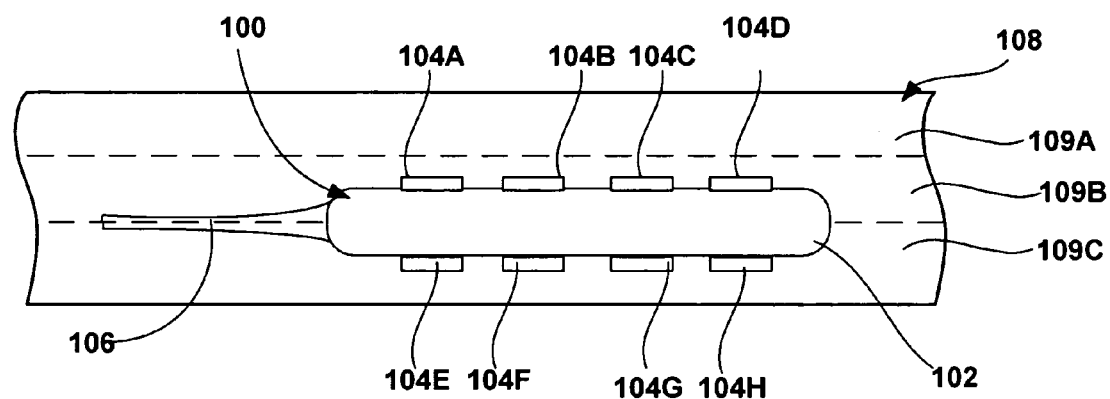
FIGS. 11A and 11B are schematic diagrams illustrating side views of example electrical stimulation leads.
Figure 11B:
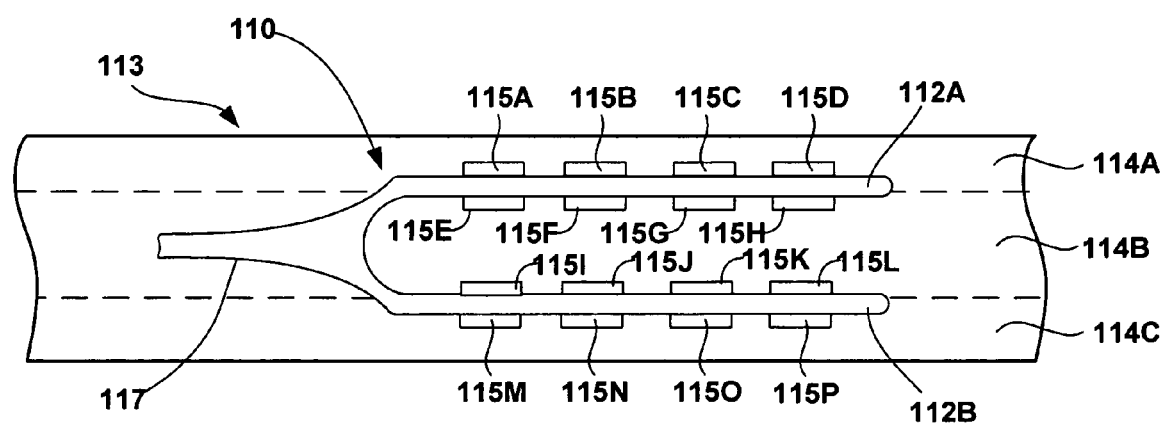

FIGS. 11A and 11B are schematics diagram illustrating side views of exemplary paddle leads that may be implanted within a patient through an introducer 88. In particular, FIG. 11A illustrates a dual sided paddle lead 30 that may be implanted within tissue of a patient, such as intra-dermal, deep dermal, or subcutaneous tissue. Dual sided paddle lead 100 includes a lead body 102 carrying electrodes 104A-H (collectively referred to as "electrodes 104") located at its distal end. Lead body 102 may be designed similar to a paddle lead design known in the field of nerve stimulation, but, as shown, carries electrodes positioned on first and second surfaces 106A and 106B (collectively "surfaces 106"), e.g., the illustrated opposing, substantially parallel, top and bottom surfaces, instead of only on one surface. Lead body 102 has a substantially flat, paddle-like shape, e.g., has a substantially oblong or rectangular cross-sectional shape.

A dual sided paddle lead 100 includes eight electrodes, i.e., electrodes 104, positioned on the top and bottom surfaces of lead body 102 for purposes of illustration. In particular, electrodes 104A-D may deliver neurostimulation to tissue 109A located shallower than lead 100 and electrodes 104E-H may deliver neurostimulation therapy to tissue 109C located deeper than lead 100. By delivering stimulation to tissue located shallower and deeper than dual sided paddle lead 100, stimulation may be delivered to a larger portion of tissue than would be possible with single sided paddle leads and, thus, may more completely ameliorate pain experienced by the patient.

FIG. 11B illustrates a multiple level lead 110 implanted within tissue 113 of a patient. Multiple level lead 110 includes a lead body 117 at its distal end comprising an upper lead body level 112A and a lower lead body level 112B (collectively "levels 112"). Upper level 112A may be located closer to the surface of the skin of the patient than lower level 112B. Upper level 112A carries electrodes 115A-D on its top surface and electrodes 115E-H on its bottom surface, and lower level 112B carries electrodes 115I-L on its top surface and electrodes 115M-P on its bottom surface. As a result, multiple level lead 110 may selectively deliver neurostimulation to any one or more of tissue 114A, 114B, and 114C. Each of electrodes 115A-P may bee electrically isolated from each other and, thus, electrode combinations may be selected to deliver stimulation to any desired one or more of tissue layers 114A, 114B, and 114C. By positioning electrodes on the top and bottom surfaces of each level, multiple level lead 110 may selectively deliver stimulation to layers of tissue and/or nerves located between any of the levels.

In the illustrated example of FIG. 11B multiple level lead 70 includes eight electrodes for the purposes of illustration. However, as previously described with respect to dual sided paddle leads in FIGS. 2A and 2B, multiple level lead 70 may include a lesser or greater number of electrodes. Again, having numerous electrodes may be particularly advantageous because the number of electrode possible combinations increases with the number of electrodes carried by the lead. In other words, providing a large number of electrode combinations increases the likelihood of discovering an electrode combination that achieves a high clinical efficacy with minimal side effects and favorable power consumption characteristics.

The invention, however, is not limited to leads 100 and 110 shown in FIGS. 11A and 11B. For example, paddle lead having any number and configuration of electrodes located on a single surface, i.e., a single sided paddle lead, may also be implanted within a patient using introducer 30. Thus, FIGS. 11A and 11B are merely exemplary and should not be considered limiting of the invention as broadly described in this disclosure.

Figure 12:
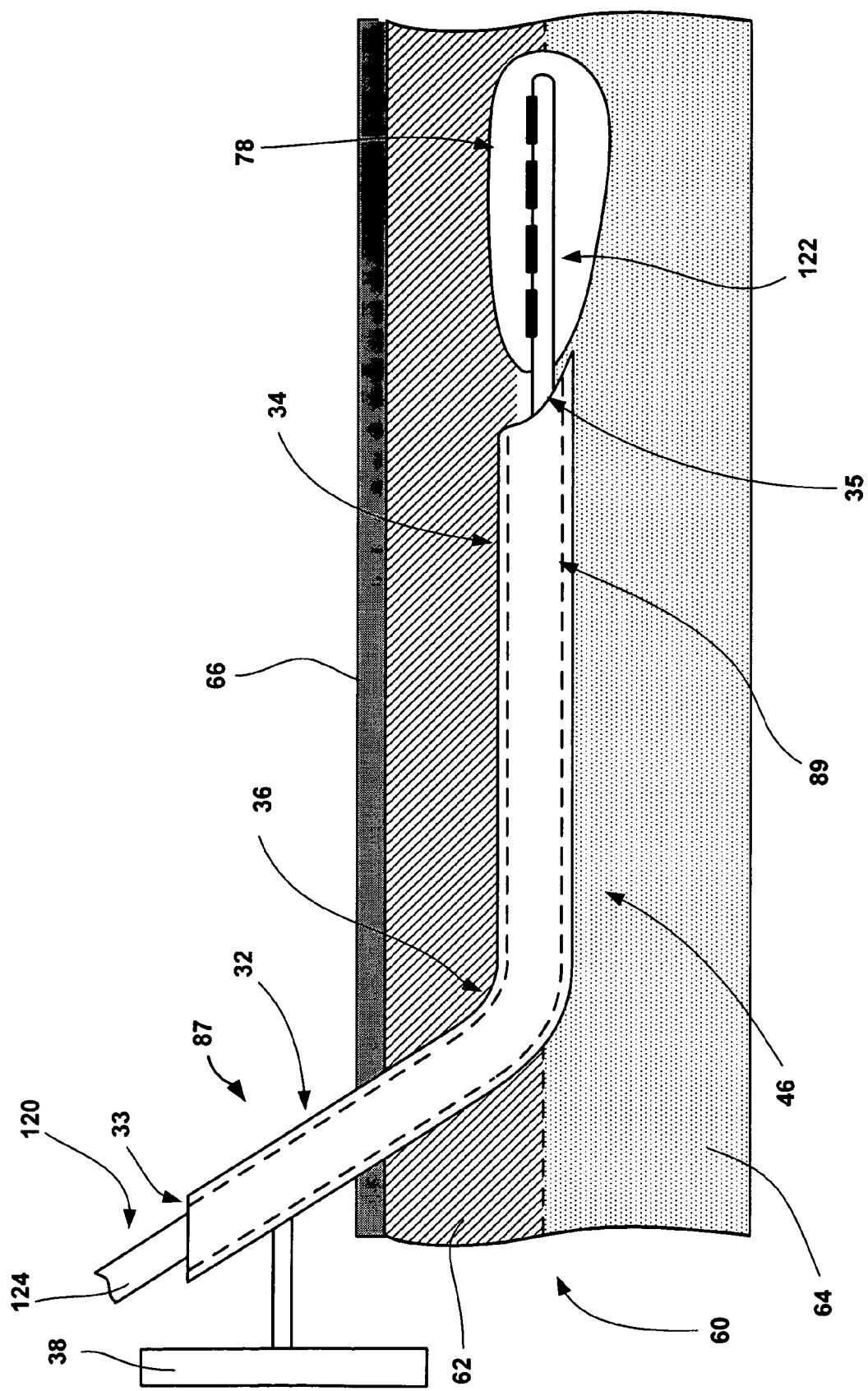
FIG. 12 is a conceptual diagram illustrating the other type of electrical stimulation lead inserted through the introducer and implanted into the patient.

FIG. 12 a cross section illustrating introducer 87 implanted between two layers of tissue 60 and paddle lead 120 implanted within space 78 through introducer 87. Paddle lead 120 may comprise a single sided paddle lead as described with respect to FIG. 9, a dual sided paddle such as dual sided paddle lead 100 in FIG. 11A, a multiple level lead such as multiple level lead 110 in FIG. 11B, or any other paddle lead or multiple level carrying electrodes on one or more surfaces.

In FIG. 12, every reference numeral associated with introducer 87 is not included in FIG. 12 to avoid confusion. In particular, longitudinal axis 43 of proximal portion 32, length 42 of proximal portion 32, longitudinal axis 45 of distal portion 34, length 40 of distal portion 34, and angle 44 are omitted from FIG. 12. However, these reference numerals are used in the description of FIG. 12 and throughout this disclosure.

In FIG. 12, paddle lead 120 is implanted within space 78 between tissue layers 62 and 64. After paddle lead 120 has been implanted as shown in FIG. 12, introducer 87 may be removed leaving paddle lead 120 implanted between layers 62 and 64 and substantially parallel to the surface of the skin 66 of the patient. As a result, paddle lead 120 may stimulate tissue and/or nerves in one or more of tissue layers 62 and 64.

Figure 13:
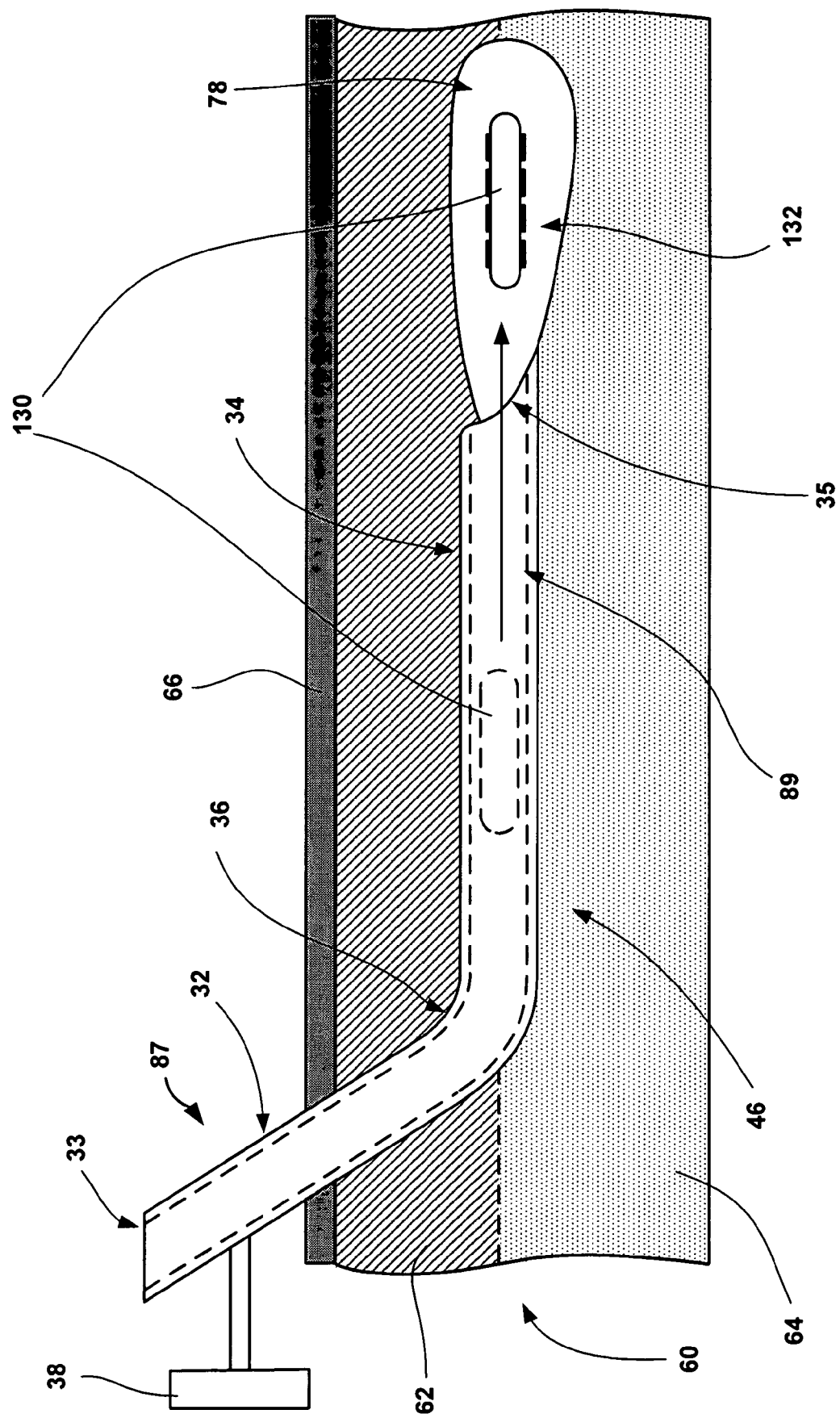
FIG. 13 is a diagram illustrating an example implantable medical device inserted through the introducer and implanted into the patient.

FIG. 13 is a cross section illustrating introducer 87 implanted between two layers of tissue 60. In particular, FIG. 13 illustrates an IMD 130 implanted between tissue layers 62 and 64. IMD 130 may include electrodes positioned on one or more surfaces of the housing. In FIG. 13, includes electrodes 132 are positioned on the top and bottom surfaces and, thus may deliver stimulation to one or more of tissue layers 62 and 64. IMD 130 may include pulse generation circuitry and deliver stimulation in the form of pulses.

To implant IMD 130 within tissue 60 a shown in FIG. 13, IMD 130 may be inserted into and through lumen 89 of introducer 87 using a tool (not shown). The tool may have a length that allows a clinician to push IMD 130 through introducer 87 to space 78 within tissue 60. The tool may be made of a relatively rigid material for application of force to IMD 130 when in the lumen of introducer 88, but may still be flexible to navigate the curved medial portion 36. An example material for such a tool is polyvinyl chloride. Alternatively, fluid may be injected into lumen 89 to advance IMD 130 through introducer 30 to space 78. In any case, a dotted outline of IMD 130 is shown in FIG. 13 to illustrate IMD 130 passing through lumen 89. Normal solid lines are used to illustrate IMD 130 implanted within tissue 60.

In FIG. 13, every reference numeral associated with introducer 88 is not included to avoid confusion. In particular, longitudinal axis 43 of proximal portion 32, length 42 of proximal portion 32, longitudinal axis 45 of distal portion 34, length 40 of distal portion 34, and angle 44 are omitted from FIG. 13. However, these reference numerals are used in the description of FIG. 13 and throughout this disclosure.

Figure 14:
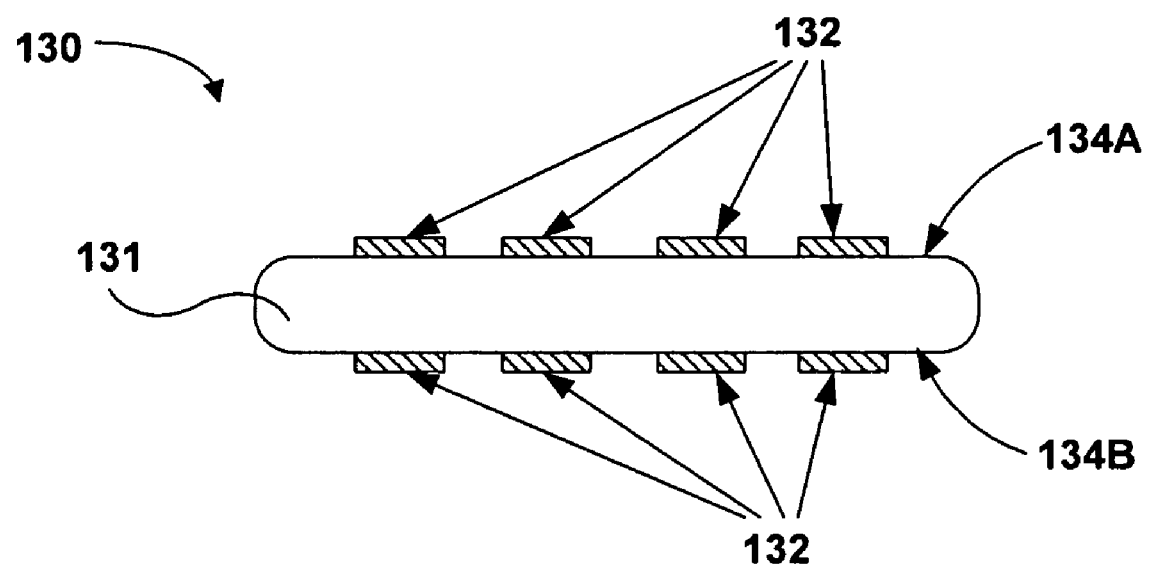
FIG. 14 is a diagram illustrating a side view of the example implantable medical device.

FIG. 14 is a diagram illustrating a side view of IMD 130. In FIG. 14, IMD 130 includes a housing 131 with a top surface 134A and a bottom surface 134B. IMD 130 also includes a plurality of electrodes 132. A first subset of electrodes 132 is located on top surface 134A, while a second subset of electrodes 132 is located on bottom surface 134B.

IMD 130 may deliver electrical stimulation, e.g., pulses, via a selected combination of electrodes 132 from one or both of top surface 134A and bottom surface 134B. As a result, IMD 130 may deliver stimulation to any one or more tissue layers. While electrodes 132 are shown located on opposing, substantially parallel surfaces 134 of housing 131, electrodes 132 may be located on adjacent surfaces of the housing, e.g., top surface 134A and one of the side surfaces of housing 131. In some alternative embodiments, electrodes 132 may be located on three or more surfaces of housing 131 or on a single surface of housing 131.

Figure 15:
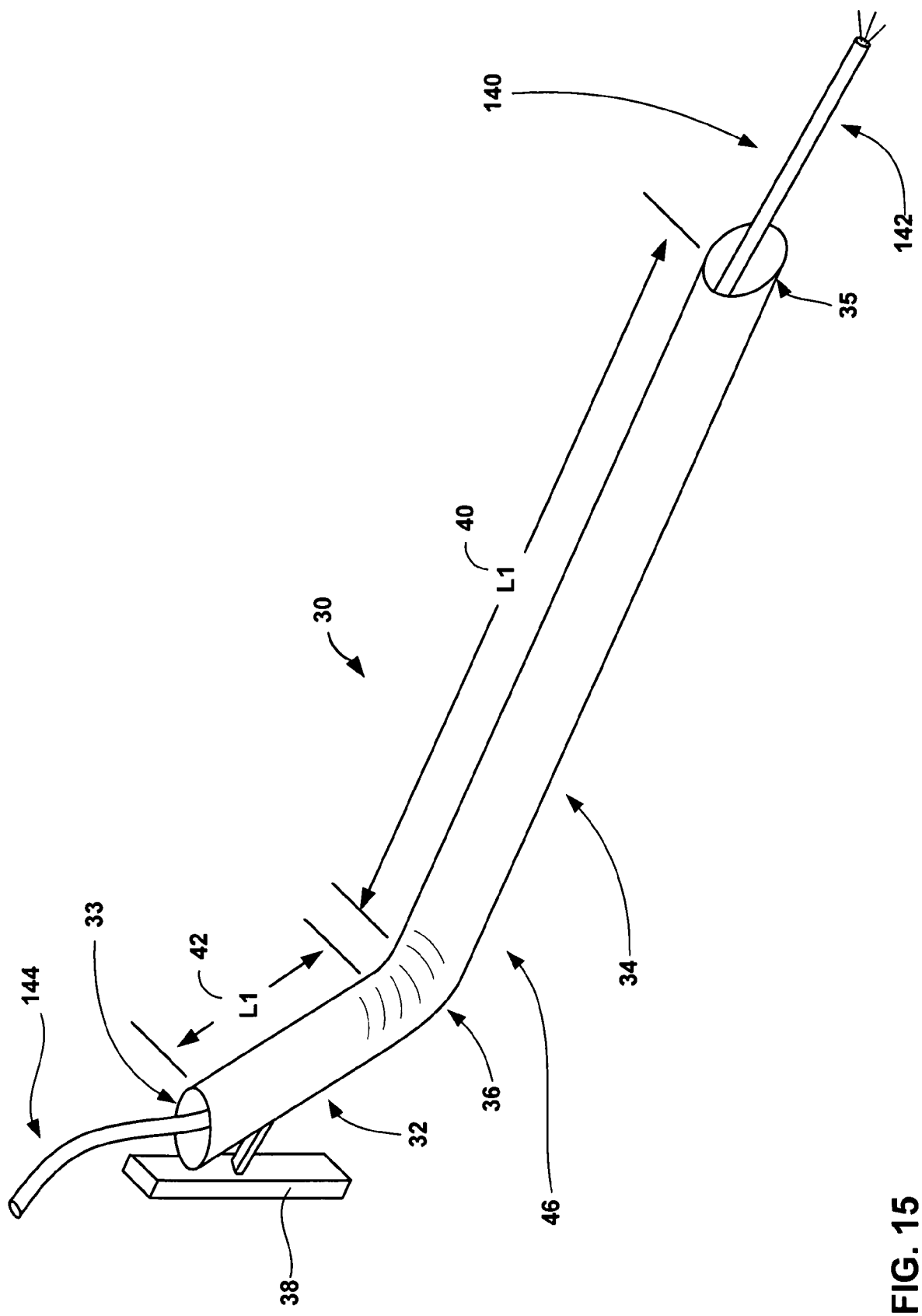
FIG. 15 is a schematic diagram illustrating an introducer to facilitate implantation of a catheter into a patient.

FIG. 15 is a schematic diagram illustrating introducer 30 that facilitates implantation of catheter 140 for delivering drug therapy to a patient. In particular, FIG. 15 illustrates catheter 140 inserted into introducer 30. Catheter 140 may be inserted into introducer 30 after introducer has been advanced to the implant site within the patient as previously described. For example, catheter 140 may be inserted such that a distal portion 142 protrudes through distal end 35 of introducer 30 and a proximal portion 144 extends through the proximal end of introducer 30 to couple catheter 140 to a drug pump (not shown).

FIG. 15 does not include every reference numeral associated with introducer 30 in order to avoid confusion. In particular, longitudinal axis 43 of proximal portion 32, longitudinal axis 45 of distal portion 34, lumen 48, and angle 44 are omitted from FIG. 15A. However, these reference numerals are used in the description of FIG. 15 and throughout this disclosure.

Figure 16:
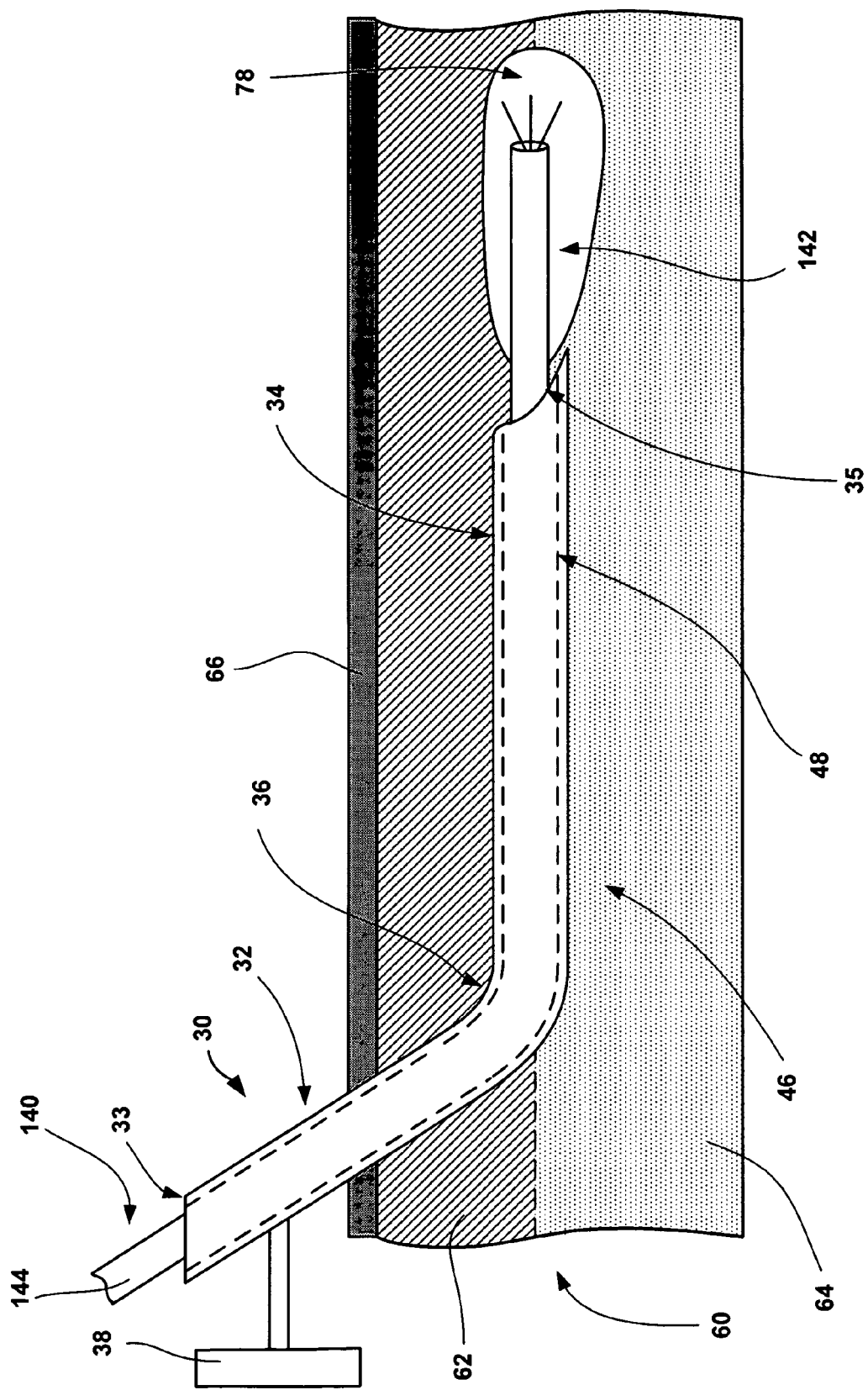
FIG. 16 is a diagram illustrating the catheter inserted through the introducer and implanted into the patient.

FIGS. 16 is a cross section illustrating introducer 30 implanted between two layers of tissue 60. In FIG. 16, catheter 140 is inserted within introducer 30 and implanted within space 78 created between tissue layers 62 and 64. Distal end 142 extends into space 78 to deliver one or more drugs to one or more of tissue layers 62 and 64. Proximal end 144 may be coupled to a drug pump.

In FIG. 16, every reference numeral associated with introducer 30 is shown. In particular, longitudinal axis 43 of proximal portion 32, length 42 of proximal portion 32, longitudinal axis 45 of distal portion 34, length 40 of distal portion 34, and angle 44 are omitted from FIG. 16.

Figure 17:
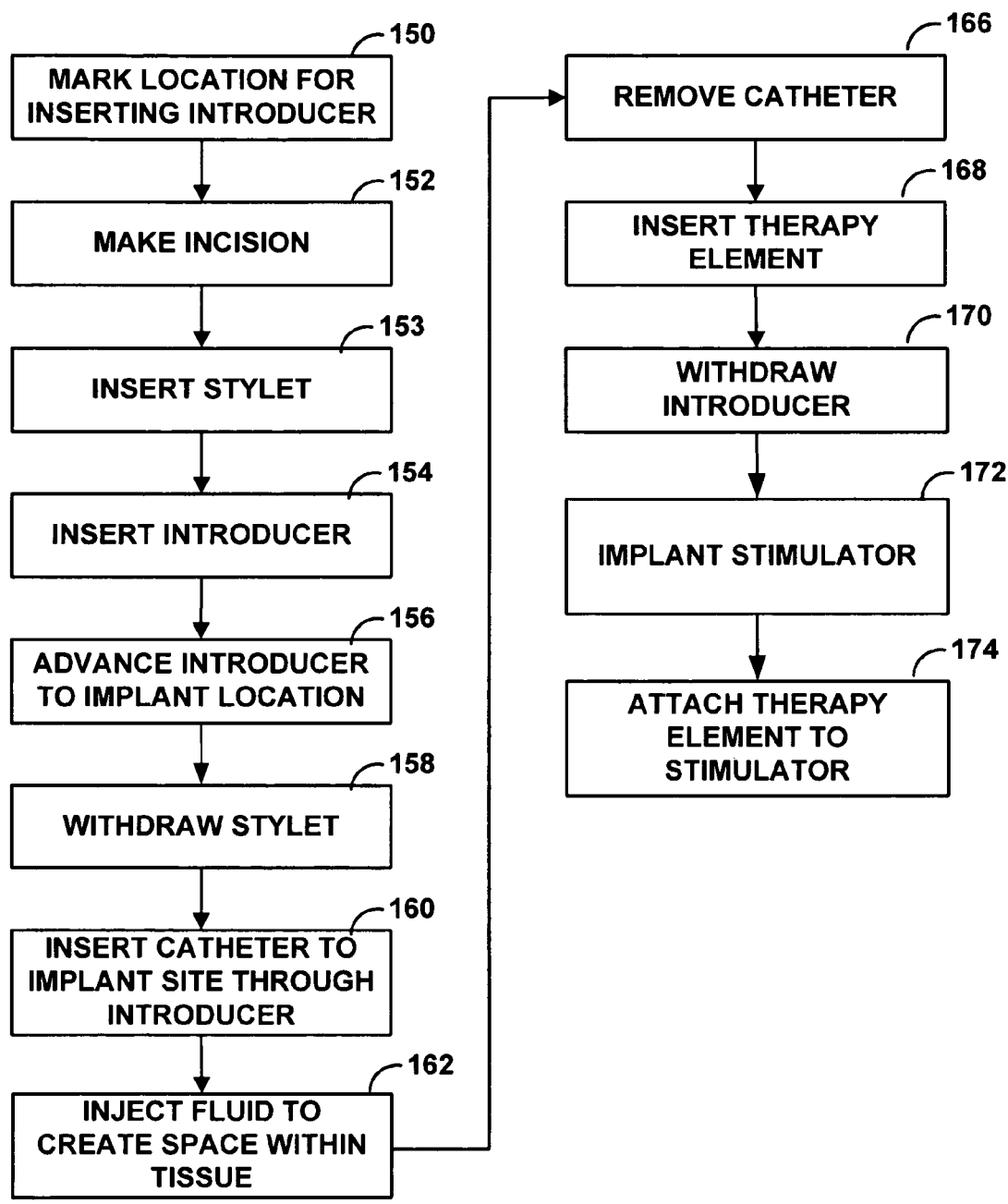
FIG. 17 is a flow diagram illustrating an example method of inserting an introducer into a patient that facilitates implantation of therapy elements within the patient.

FIG. 17 is a flow diagram illustrating an example method for percutaneously inserting a therapy element using introducer 30. Although described with respect to introducer 30, the method may be used with introducer 88 or any introducer according to the invention. Initially, a physician may mark a location on the patient for inserting introducer 30 (150) and makes an incision at the marked location (152) to ease insertion of introducer 30. To prevent tissue coring and assist in tissue dissection, the physician may insert stylet 50 (153). Stylet 50 may be sized to substantially fill lumen 48 and have a tapered distal end 52 as shown in FIGS. 4 and 5. When stylet 50 is inserted into introducer 30, the physician inserts introducer 30 (154) at the incision.

After introducer 30 has been inserted into the patient, the physician may advance the distal end of the introducer 30 to the implant site (156). As an example, the physician may insert introducer 30 at an angle and advance introducer 30 to the desired dermal depth of the implant site. The physician may grasp proximal portion 54 of stylet 50 or handle 30 protruding from proximal portion 32 of introducer 30 to control insertion and advancement of introducer 30.

When distal tip 35 of introducer 30 is at the correct dermal depth, the physician may manipulate the skin of the patient and change the angle of insertion in order to follow the dermal depth to the implant site. The angle of the proximal portion 32 with respect to distal portion 34 may facilitate such manipulation. The shape of introducer 30 may allow the physician to more easily follow the dermal depth. In other words, having curved portion 36 medially located between substantially straight proximal and distal portions 32, 34 may allow the physician to more easily advance introducer 30 substantially parallel to the skin of the patient, e.g., within a layer of tissue or between layers of tissue. For example, angle 44 of curved portion 36 may allow the physician to apply force along or substantially parallel to the skin of the patient. In this manner, the distal portion 34 of introducer 30 may be inserted substantially parallel to the skin of the patient when the physician has fully advanced introducer 30 to the implant site.

After introducer 30 has been inserted to the implant site, the physician may withdraw stylet 50 (158) and insert catheter 70 to the implant site through introducer 30 (160). The physician may insert catheter 70 to inject fluid to create space 78 within tissue 60 (162) for implanting a therapy element. As shown in FIGS. 6 and 7, catheter 70 may be coupled to fluid source 76 that pumps fluid, such as saline or other biocompatible fluid, to the implant site via catheter 70. In other embodiments, fluid may be inserted without a catheter or the benefit of a non-manual pump, as described above. In yet other embodiments, catheter 70 may be inserted to the implant side independent of introducer 30. In other words, catheter 70 is not inserted to the implant site through introducer 30. Instead, catheter 70 may be inserted to the implant site through a different incision or needlestick. In this case, fluid may be injected continuously as a therapy element is inserted through introducer 30 as previously described.

After injecting fluid to create space 78 the physician may remove catheter 70 (166) and insert a therapy element, e.g., a distal portion of the therapy element, into space 78 (168). In embodiments in which catheter 70 is inserted to the implant site outside of introducer 30, the physician may insert a therapy element while catheter 70 injects fluid to create space 78 within the tissue. In any case, the therapy element may comprise any therapy element illustrated in FIGS. 1-16, although the invention is not limited as such.

After inserting the therapy element, the physician may withdraw introducer 30 (170) leaving the therapy element implanted within the patient. As previously described, introducer 30 may facilitate implanting the therapy element substantially parallel to the skin of the patient, e.g., within a layer of tissue or between layers of tissue.

In some embodiments, fluid source 76 may be operated in reverse, or some other vacuum source may be used to evacuate fluid and loose tissue after the therapy element has been implanted. The loose tissue may comprise tissue damaged during implantation of introducer 30, tissue damaged when injecting fluid to create space 78, or both.

The physician may then implant a stimulator (172) just below the skin of the patient. In particular, the physician implants a stimulator if the therapy element delivers electrical stimulation to the patient. However, if the therapy element comprises, for example, a catheter for delivering drug therapy, the physician may implant a drug pump. In any case, the stimulator or drug pump may be implanted in a region of the patient's body that can accommodate such a device. For example, if the therapy element comprises a lead for delivering stimulation to an axial region of the patient's back, the stimulator may be implanted in a subcutaneous pocket in the lower back of the patient. If the therapy element comprises a lead for delivering stimulation within various regions of the back of the head, above the eyebrow, over the eye, or under the eye, the stimulator may be implanted in a subcutaneous pocket in the neck or back of the head. In any case, after the stimulator is implanted, the physician may attach or couple the therapy element to the stimulator (174), for example, by tunneling the proximal end of the therapy element through tissue to the stimulator.

Various embodiments of the invention have been described. One of ordinary skill will appreciate that various modifications may be made to the described embodiments without departing from the scope of the invention. These and other embodiments are within the scope of the following claims.

The invention claimed is:

1. A device to facilitate implantation of a therapy element into a patient comprising an elongated body having a proximal end and a distal end for insertion into tissue of the patient,
   wherein the elongated body defines a lumen sized for insertion of the therapy element from the proximal end to the distal end through the lumen,
   wherein the elongated body comprises a substantially straight and substantially rigid proximal portion, a substantially straight and substantially rigid distal portion, and a curved portion located between the proximal portion and the distal portion, the curved portion less rigid than the proximal and distal portions, and
   wherein a length of the distal portion as measured from the distal end to the curved portion is greater than or approximately equal to a length of the proximal portion as measured from the curved portion to the proximal end,
   wherein the length of the distal portion is at least approximately twice the length of the proximal portion.

2. The device of claim 1, wherein the curved portion is located closer to the proximal end of the elongated body than the distal end of the elongated body.

3. The device of claim 1, wherein the curved portion defines an angle between a longitudinal axis of the proximal portion and a longitudinal axis of the distal portion, the angle within a range of approximately twenty degrees to approximately sixty degrees.

4. The device of claim 1, wherein the lumen is sized to receive at least one of an implantable medical device, an implantable medical lead, or a catheter.

5. A kit to facilitate implantation of therapy elements into a patient comprising:
   a therapy element; and
   an introducer comprising an elongated body having a proximal end and a distal end for insertion into tissue of the patient,
   wherein the elongated body defines a lumen sized for advancement of the therapy element from the proximal end to the distal end through the lumen,
   wherein the elongated body comprises a substantially straight and substantially rigid proximal portion, a substantially straight and substantially rigid distal portion, and a curved portion located between the proximal portion and the distal portion, the curved portion less rigid than the proximal and distal portions, and
   wherein a length of the distal portion as measured from the distal end to the curved portion is greater than or approximately equal to a length of the proximal portion as measured from the curved portion to the proximal end,
   wherein the length of the distal portion is at least approximately twice the length of the proximal portion.

6. The kit of claim 5, wherein the curved portion defines an angle between a longitudinal axis of the proximal portion and a longitudinal axis of the distal portion, the angle within a range of approximately twenty degrees to approximately sixty degrees.

7. The kit of claim 5, wherein the therapy element comprises at least one of an implantable medical device, an implantable medical lead, or a catheter.

8. The kit of claim 5, wherein the therapy element comprises an implantable medical device that includes a housing having one or more electrodes.

9. The kit of claim 5, further comprising a stylet sized to pass through the lumen from the proximal end of the elongated body to the distal end of the elongated body, wherein a distal end of the stylet is tapered to an edge for dissecting tissue when the introducer is inserted into the patient with the distal end of the stylet located within the lumen.

10. A kit to facilitate implantation of therapy elements into a patient comprising:
   a therapy element;
   an introducer comprising an elongated body having a proximal end and a distal end for insertion into tissue of the patient,
   wherein the elongated body defines a lumen sized for advancement of the therapy element from the proximal end to the distal end through the lumen,
   wherein the elongated body comprises a substantially straight and substantially rigid proximal portion, a substantially straight and substantially rigid distal portion, and a curved portion located between the proximal portion and the distal portion, the curved portion less rigid than the proximal and distal portions, and
   wherein a length of the distal portion as measured from the distal end to the curved portion is greater than or approximately equal to a length of the portion as measured from the curved portion to the proximal end; and
   a fluid source that delivers fluid proximate to the distal end of the elongated body through the lumen of the elongated body to create a space within tissue of the patient.

11. The kit of claim 10, further comprising a vacuum source that evacuates fluid from the space.

12. A method comprising:
   inserting an introducer into a patient, the introducer comprising an elongated body having a proximal end and a distal end for insertion into tissue of the patient, the elongated body defining a lumen;
   advancing the distal end of the elongated body through tissue of the patient to a position within the patient proximate to a therapy delivery site;
   advancing a therapy element from the proximal end of the elongated body to the distal end of the elongated body through the lumen to implant the therapy element at the therapy delivery site,
   wherein the elongated body comprises a substantially straight and substantially rigid proximal portion, a substantially straight and substantially rigid distal portion, and a curved portion located between the proximal portion and the distal portion, the curved portion less rigid than the proximal and distal portions, and
   wherein a length of the distal portion as measured from the distal end to the curved portion is greater than or approximately equal to a length of the proximal portion as measured from the curved portion to the proximal end; and
   introducing fluid into the implantation site through the lumen defined by the elongated body to create a space for implanting the therapy element.

13. The method of claim 12, wherein advancing the distal end of the elongated body comprising advancing the distal end substantially parallel to a surface of skin of the patient.

14. The method of claim 12, wherein inserting the introducer comprises inserting the introducer such that the distal end of the elongated body is substantially positioned between two layers of tissue of the patient, advancing the distal end comprises advancing the distal end substantially between the layers to a position proximate to a therapy delivery site and between the layers, and advancing the therapy element comprises advancing the therapy element to implant the therapy element substantially between the layers at the therapy delivery site.

15. The method of claim 14, wherein the layers comprise two of an intra-dermal, deep dermal, or subcutaneous tissue layer of the patient.

16. The method of claim 14,
   wherein inserting the introducer comprises:
      inserting a stylet through the lumen such that a distal end of the stylet is located at the distal end of the elongated body; and
      inserting the introducer with the distal end of the stylet located at the distal end of the elongated body, wherein the distal end of the stylet is tapered to an edge, and
   wherein advancing the distal end of the elongated body through tissue of the patient comprise dissecting the tissue between the layers with the edge of the introducer.

17. The method of claim 12, wherein introducing fluid to create a space comprises introducing fluid to separate layers of tissue of the patient.

18. The method of claim 17, wherein the layers comprise two of an intra-dermal, deep dermal, or subcutaneous tissue layer of the patient.

19. The method of claim 12, wherein introducing a therapy element comprises introducing at least one at least one of an implantable medical device, an implantable medical lead, or a catheter.

20. The method of claim 12, wherein introducing a therapy element comprises introducing an implantable medical device that includes a housing having one or more electrodes.

21. The device of claim 1, further comprising a handle protruding from the proximal portion for the application of force in the direction of advancement of the distal portion within the patient.

22. The kit of claim 5, further comprising a handle protruding from the proximal portion for the application of force in the direction of advancement of the distal portion within the patient.

23. The kit of claim 5, wherein the elongated body defines a continuous and smooth external surface that extends over the substantially straight and substantially rigid proximal portion, the substantially straight and substantially rigid distal portion, and the curved portion located between the proximal portion and the distal portion.

24. The device of claim 1, wherein the elongated body defines a continuous and smooth external surface that extends over the substantially straight and substantially rigid proximal portion, the substantially straight and substantially rigid distal portion, and the curved portion located between the proximal portion and the distal portion.

* * * * *